US006130062A

United States Patent [19]

Milland et al.

[11] Patent Number: 6,130,062

[45] Date of Patent: Oct. 10, 2000

[54] PRODUCTION OF PROTEINS IN HOST CELLS

[75] Inventors: Julie Milland, Northcote; Bruce Loveland, Ashburton; Dale Christiansen, Eltham; Ian F. C. McKenzie, Brunswick, all of Australia

[73] Assignee: The Austin Research Institute, Heidelberg, Australia

[21] Appl. No.: 08/793,418

[22] PCT Filed: Aug. 30, 1995

[86] PCT No.: PCT/AU95/00553

§ 371 Date: Feb. 25, 1997

§ 102(e) Date: Feb. 25, 1997

[87] PCT Pub. No.: WO96/06937

PCT Pub. Date: Mar. 7, 1996

[30] Foreign Application Priority Data

Aug. 30, 1994 [AU] Australia ............................... PM 7724

[51] Int. Cl.[7] ........................... C12N 15/67; C12N 15/79; C12N 5/10; C12N 15/12

[52] U.S. Cl. ..................... 435/69.1; 435/91.42; 435/455; 435/320.1; 536/23.5

[58] Field of Search ............................... 435/69.1, 91.41, 435/91.42, 455, 320.1; 536/23.5

[56] References Cited

FOREIGN PATENT DOCUMENTS

| | | | |
|---|---|---|---|
| 0385962 | 5/1990 | European Pat. Off. | C12N 15/82 |
| WO 93/20212 | 10/1993 | WIPO | C12N 15/67 |

OTHER PUBLICATIONS

Lusky et al. Inhibition of SV40 replication in simian cells by specific pBR322 DNA sequences. Nature vol. 293 pp. 79–81, 1981.

*Primary Examiner*—John S. Brusca
*Attorney, Agent, or Firm*—Limbach & Limbach LLP

[57] ABSTRACT

Method of increasing protein production in a host cell where the nucleic acid encoding the protein has an A and/or T rich region in an exon. The method comprising lowering the amount of A and/or T rich region and transfecting a host cell with the altered nucleic acid and obtaining expression of the nucleic acid. The invention also relates to the recombinant nucleic acid constructs, purified protein preparations and pharmaceutical compositions produced as well as methods of treatment utilizing the purified protein preparation.

18 Claims, 10 Drawing Sheets

```
                SCR1 | SCR2
               C  Y  R |E  T  C   P  Y  I  R   D  P  L   N  G  Q   A  V  P  A   N  G  T   Y  E  F   G  Y  Q  M
wt SCR     TGTTATAGA GAAACATGTC CATATATACG GGATCCTTTA AATGGCCAAG CAGTCCCTGC AAATGGGACT TACGAGTTTG GTTATCAGAT  89
subSCR2    ......... .......... .......... .......... .......... .......... .......... .......... ..........  401
subSCR3    ......... .......... .......... .......... .......... .......... .......... .......... ..........
subSCR2+3  ......... .......... .......... .......... .......... .......... .......... .......... ..........
delSCR2/   ........[DELETION OF SCR2 →]
subSCR3

               H  F I  C  N  E  G  Y  Y  L   I  G  E   E  I  L   Y  C  E  L   K  G  S   V  A  I  W  S  G  K
wt SCR     GCACTTTATT TGTAATGAGG GTTATTACTT AATTGGTGAA GAAATTCTAT ATTGTGAACT TAAAGGATCA GTAGCAATTT GGAGCGGTAA  119
subSCR2    ......C..C ..C..C.... ....C...C. G........G ..G..C..G. .......... .......... .......... ..........  491
subSCR3    .......... .......... .......... .......... .......... .......... .......... .......... ..........
subSCR2+3  ......C..C ..C..C.... ....C...C. G........G ..G..C..G. .......... .......... .......... ..........
delSCR2/        [→ SCR2 DELETION →]
subSCR3

                          SCR2 | SCR3
               P  P  I  C  E  K |V  L  C  T   P  P  P   K  I  K   N  G  K  H   T  F  S   E
wt SCR     GCCCCCAATA TGTGAAAAGG TTTTGTGTAC ACCACCTCCA AAAATAAAAA ATGGAAAACA CACCTTTAGT GAA  143
subSCR2    .......... .......... .......... .......... .......... .......... .......... ...  564
subSCR3    .......... .....G.... .C........ .......... ..G..C..G. .......... .......... ...
subSCR2+3  .......... .....G.... .C........ .......... ..G..C..G. .......... .......... ...
delSCR2/     [ DELETION → ]   .. .C........ .......... ..G..C..G. .......... .......... ...
subSCR3
```

FIG. 1

SEQUENCE LISTING

<160> NUMBER OF SEQ ID NOS: 15

<210> SEQ ID NO 1
<211> LENGTH: 1134
<212> TYPE: DNA
<213> ORGANISM: Artificial Sequence
<220> FEATURE:
<223> OTHER INFORMATION: Description of Artificial Sequence: CD46 cDNA
sequence with wild type SCR

<400> SEQUENCE: 1

```
atggagcctc ccggccgccg cgagtgtccc tttccttcct ggcgctttcc tgggttgctt     60

ctggcggcca tggtgttgct gctgtactcc ttctccgatg cctgtgagga gccaccaaca    120

tttgaagcta tggagctcat tggtaaacca aaaccctact atgagattgg tgaacgagta    180

gattataagt gtaaaaaagg atacttctat atacctcctc ttgccaccca tactatttgt    240

gatcggaatc atacatggct acctgtctca gatgacgcct gttatagaga aacatgtcca    300

tatatacggg atcctttaaa tggccaagca gtccctgcaa atgggactta cgagtttggt    360

tatcagatgc actttatttg taatgagggt tattacttaa ttggtgaaga aattctatat    420

tgtgaactta aaggatcagt agcaatttgg agcggtaagc cccaatatg tgaaaaggtt     480

ttgtgtacac cacctccaaa aataaaaaat ggaaaacaca cctttagtga agtagaagta    540

tttgagtatc ttgatgcagt aacttatagt tgtgatcctg cacctggacc agatccattt    600

tcacttattg gagagagcac gatttattgt ggtgacaatt cagtgtggag tcgtgctgct    660

ccagagtgta aagtggtcaa atgtcgattt ccagtagtcg aaaatggaaa acagatatca    720

ggatttggaa aaaaatttta ctacaaagca acagttatgt ttgaatgcga taagggtttt    780

tacctcgatg gcagcgacac aattgtctgt gacagtaaca gtacttggga tcccccagtt    840

ccaaagtgtc ttaaagtgtc gacttcttcc actacaaaat ctccagcgtc cagtgcctca    900

ggtcctaggc ctacttacaa gcctccagtc tcaaattatc caggatatcc taaacctgag    960

gaaggaatac ttgacagttt ggatgtttgg gtcattgctg tgattgttat tgccatagtt   1020

gttggagttg cagtaatttg tgttgtcccg tacagatatc ttcaaaggag gaagaagaaa   1080

ggcacatacc taactgatga gacccacaga gaagtaaaat ttacttctct ctga         1134
```

<210> SEQ ID NO 2
<211> LENGTH: 1134
<212> TYPE: DNA
<213> ORGANISM: Artificial Sequence
<220> FEATURE:
<223> OTHER INFORMATION: Description of Artificial Sequence: CD46 cDNA
subSCR2 variant

<400> SEQUENCE: 2

```
atggagcctc ccggccgccg cgagtgtccc tttccttcct ggcgctttcc tgggttgctt     60

ctggcggcca tggtgttgct gctgtactcc ttctccgatg cctgtgagga gccaccaaca    120

tttgaagcta tggagctcat tggtaaacca aaaccctact atgagattgg tgaacgagta    180

gattataagt gtaaaaaagg atacttctat atacctcctc ttgccaccca tactatttgt    240

gatcggaatc atacatggct acctgtctca gatgacgcct gttatagaga aacatgtcca    300

tatatacggg atcctttaaa tggccaagca gtccctgcaa atgggactta cgagtttggt    360

tatcagatgc actctacttg caacgagggt tactacctga ttggtgagga gatcctgtat    420

tgtgaactta aaggatcagt agcaatttgg agcggtaagc cccaatatg tgaaaaggtt     480
```

-continued

```
ttgtgtacac cacctccaaa aataaaaaat ggaaaacaca cctttagtga agtagaagta    540

tttgagtatc ttgatgcagt aacttatagt tgtgatcctg cacctggacc agatccattt    600

tcacttattg gagagagcac gatttattgt ggtgacaatt cagtgtggag tcgtgctgct    660

ccagagtgta aagtggtcaa atgtcgattt ccagtagtcg aaaatggaaa acagatatca    720

ggatttggaa aaaaatttta ctacaaagca acagttatgt ttgaatgcga taagggtttt    780

tacctcgatg gcagcgacac aattgtctgt gacagtaaca gtacttggga tcccccagtt    840

ccaaagtgtc ttaaagtgtc gacttcttcc actacaaaat ctccagcgtc cagtgcctca    900

ggtcctaggc ctacttacaa gcctccagtc tcaaattatc caggatatcc taaacctgag    960

gaaggaatac ttgacagttt ggatgtttgg gtcattgctg tgattgttat tgccatagtt   1020

gttggagttg cagtaatttg tgttgtcccg tacagatatc ttcaaaggag gaagaagaaa   1080

ggcacatacc taactgatga gacccacaga gaagtaaaat ttacttctct ctga         1134
```

<210> SEQ ID NO 3
<211> LENGTH: 1134
<212> TYPE: DNA
<213> ORGANISM: Artificial Sequence
<220> FEATURE:
<223> OTHER INFORMATION: Description of Artificial Sequence: CD46 cDNA subSCR3 variant

<400> SEQUENCE: 3

```
atggagcctc ccggccgccg cgagtgtccc tttccttcct ggcgctttcc tgggttgctt     60

ctggcggcca tggtgttgct gctgtactcc ttctccgatg cctgtgagga gccaccaaca    120

tttgaagcta tggagctcat tggtaaacca aaaccctact atgagattgg tgaacgagta    180

gattataagt gtaaaaaagg atacttctat atacctcctc ttgccaccca tactatttgt    240

gatcggaatc atacatggct acctgtctca gatgacgcct gttatagaga aacatgtcca    300

tatatacggg atcctttaaa tggccaagca gtccctgcaa atgggactta cgagtttggt    360

tatcagatgc actttatttg taatgagggt tattacttaa ttggtgaaga aattctatat    420

tgtgaactta aaggatcagt agcaatttgg agcggtaagc cccccaatatg tgaaaaggtt    480

ttgtgtacac cacctccaaa gatcaagaat ggaaaacaca cctttagtga agtagaagta    540

tttgagtatc ttgatgcagt aacttatagt tgtgatcctg cacctggacc agatccattt    600

tcacttattg gagagagcac gatttattgt ggtgacaatt cagtgtggag tcgtgctgct    660

ccagagtgta aagtggtcaa atgtcgattt ccagtagtcg aaaatggaaa acagatatca    720

ggatttggaa aaaaatttta ctacaaagca acagttatgt ttgaatgcga taagggtttt    780

tacctcgatg gcagcgacac aattgtctgt gacagtaaca gtacttggga tcccccagtt    840

ccaaagtgtc ttaaagtgtc gacttcttcc actacaaaat ctccagcgtc cagtgcctca    900

ggtcctaggc ctacttacaa gcctccagtc tcaaattatc caggatatcc taaacctgag    960

gaaggaatac ttgacagttt ggatgtttgg gtcattgctg tgattgttat tgccatagtt   1020

gttggagttg cagtaatttg tgttgtcccg tacagatatc ttcaaaggag gaagaagaaa   1080

ggcacatacc taactgatga gacccacaga gaagtaaaat ttacttctct ctga         1134
```

<210> SEQ ID NO 4
<211> LENGTH: 1134
<212> TYPE: DNA
<213> ORGANISM: Artificial Sequence
<220> FEATURE:
<223> OTHER INFORMATION: Description of Artificial Sequence: CD46 cDNA -continued subSCR2+3 variant

<400> SEQUENCE: 4
atggagcctc ccggccgccg cgagtgtccc tttccttcct ggcgctttcc tgggttgctt 60
ctggcggcca tggtgttgct gctgtactcc ttctccgatg cctgtgagga gccaccaaca 120
tttgaagcta tggagctcat tggtaaacca aaaccctact atgagattgg tgaacgagta 180
gattataagt gtaaaaaagg atacttctat atacctcctc ttgccaccca tactatttgt 240
gatcggaatc atacatggct acctgtctca gatgacgcct gttatagaga aacatgtcca 300
tatatacggg atcctttaaa tggccaagca gtccctgcaa atgggactta cgagtttggt 360
tatcagatgc actctacttg caacgagggt tactacctga ttggtgagga gatcctgtat 420
tgtgaactta aaggatcagt agcaatttgg agcggtaagc cccaatatg tgaaaaggtt 480 ttgtgtacac cacctccaaa gatcaagaat ggaaaacaca cctttagtga agtagaagta 540
tttgagtatc ttgatgcagt aacttatagt tgtgatcctg cacctggacc agatccattt 600
tcacttattg gagagagcac gatttattgt ggtgacaatt cagtgtggag tcgtgctgct 660
ccagagtgta aagtggtcaa atgtcgattt ccagtagtcg aaaatggaaa acagatatca 720
ggatttggaa aaaaatttta ctacaaagca acagttatgt ttgaatgcga taagggtttt 780
tacctcgatg gcagcgacac aattgtctgt gacagtaaca gtacttggga tcccccagtt 840
ccaaagtgtc ttaaagtgtc gacttcttcc actacaaaat ctccagcgtc cagtgcctca 900
ggtcctaggc ctacttacaa gcctccagtc tcaaattatc caggatatcc taaacctgag 960
gaaggaatac ttgacagttt ggatgtttgg gtcattgctg tgattgttat tgccatagtt 1020
gttggagttg cagtaatttg tgttgtcccg tacagatatc ttcaaaggag gaagaagaaa 1080
ggcacatacc taactgatga gacccacaga gaagtaaaat ttacttctct ctga 1134

<210> SEQ ID NO 5
<211> LENGTH: 945
<212> TYPE: DNA
<213> ORGANISM: Artificial Sequence
<220> FEATURE:
<223> OTHER INFORMATION: Description of Artificial Sequence: CD46 cDNA
delSCR2/subSCR3 variant

<400> SEQUENCE: 5
atggagcctc ccggccgccg cgagtgtccc tttccttcct ggcgctttcc tgggttgctt 60
ctggcggcca tggtgttgct gctgtactcc ttctccgatg cctgtgagga gccaccaaca 120
tttgaagcta tggagctcat tggtaaacca aaaccctact atgagattgg tgaacgagta 180
gattataagt gtaaaaaagg atacttctat atacctcctc ttgccaccca tactatttgt 240
gatcggaatc atacatggct acctgtctca gatgacgcct gttatagggt cttgtgtaca 300
ccacctccaa agatcaagaa tggaaaacac acctttagtg aagtagaagt atttgagtat 360
cttgatgcag taacttatag ttgtgatcct gcacctggac cagatccatt ttcacttatt 420
ggagagagca cgatttattg tggtgacaat tcagtgtgga gtcgtgctgc tccagagtgt 480
aaagtggtca aatgtcgatt tccagtagtc gaaaatggaa aacagatatc aggatttgga 540
aaaaaatttt actacaaagc aacagttatg tttgaatgcg ataagggttt ttacctcgat 600
ggcagcgaca caattgtctg tgacagtaac agtacttggg atcccccagt tccaaagtgt 660
cttaaagtgt cgacttcttc cactacaaaa tctccagcgt ccagtgcctc aggtcctagg 720
cctacttaca agcctccagt ctcaaattat ccaggatatc ctaaacctga ggaaggaata 780

-continued cttgacagtt tggatgtttg ggtcattgct gtgattgtta ttgccatagt tgttggagtt 840
gcagtaattt gtgttgtccc gtacagatat cttcaaagga ggaagaagaa aggcacatac 900
ctaactgatg agacccacag agaagtaaaa tttacttctc tctga 945

<210> SEQ ID NO 6
<211> LENGTH: 84
<212> TYPE: PRT
<213> ORGANISM: Artificial Sequence
<220> FEATURE:
<223> OTHER INFORMATION: Description of Artificial Sequence: peptide encoded by nucleic acids 280-531 of SEQ ID NO:1

<400> SEQUENCE: 6

```
Cys Tyr Arg Glu Thr Cys Pro Tyr Ile Arg Asp Pro Leu Asn Gly Gln
  1               5                  10                  15

Ala Val Pro Ala Asn Gly Thr Tyr Glu Phe Gly Tyr Gln Met His Phe
             20                  25                  30

Ile Cys Asn Glu Gly Tyr Tyr Leu Ile Gly Glu Glu Ile Leu Tyr Cys
         35                  40                  45

Glu Leu Lys Gly Ser Val Ala Ile Trp Ser Gly Lys Pro Pro Ile Cys
     50                  55                  60

Glu Lys Val Leu Cys Thr Pro Pro Pro Lys Ile Lys Asn Gly Lys His
 65                  70                  75                  80

Thr Phe Ser Glu
```

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 7
caatcaggta gtaaccctcg ttgcagatga agtgcatc 38

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 8
cggaattcac agcgtcttcc gcgccgcgc 29

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 9
ggtcttgtgt acaccacctc caaagatcaa gaatggaaaa c 41

<210> SEQ ID NO 10
<211> LENGTH: 27

-continued

<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 10
agcaatgacc taaacatcca aactgtc 27

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 11
tggatgttta ggtcattgct gtgatt 26

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 12
ggtgtacaca agaccttata acaggcgtca tctg 34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 13
acgaattcga tttcaagcca ctttctttac aaag 34

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: oligonucleotide primer for generating altered CD46 construct

<400> SEQUENCE: 14
ggtggtgtac acaagacctt ctcacatatt gg 32

<210> SEQ ID NO 15
<211> LENGTH: 44
<212> TYPE: DNA
<213> ORGANISM: Artificial Sequence
<220> FEATURE:

-continued

```
<223> OTHER INFORMATION: Description of Artificial Sequence:
      oligonucleotide primer for generating altered CD46
      construct

<400> SEQUENCE: 15

cgagggttac tacctgattg gtgaggagat cctgtattgt gaac                   44
```

PRODUCTION OF PROTEINS IN HOST CELLS

FIELD OF THE INVENTION

The present invention relates generally to improved production of proteins in host cells. In particular it relates to improved production of proteins which are required for therapeutic or reagent applications and which are difficult to obtain in sufficient quantities. The invention also relates to a method of producing recombinant nucleic acid molecules which encode said proteins, to the recombinant nucleic acid molecules and recombinant constructs comprising the same and to the proteins produced thereby. Of particular interest are nucleic acid molecules encoding hormones, cytokines, growth factors, receptors and their ligands and cell surface proteins including complement regulating proteins.

BACKGROUND OF THE INVENTION

Although many genes and cDNAs encoding useful proteins have been isolated, a major problem facing scientists is the production of sufficient amounts of recombinant proteins for further study and for diagnostic or therapeutic applications. This is particularly so where commercial production of the protein is desired. In particular the production of hormones, cytokines, growth factors, receptors and their ligands and other proteins by recombinant means has become a major endeavour.

By way of example the cell surface molecule, CD46 (also known as membrane cofactor or MCP) has not been expressed in eukaryotic hosts as well as other cDNA constructs using a variety of expression vectors. Similar concerns have arisen about CD55 (DAF) and CD35 (CR1) and factor H which like CD46, are members of the family of proteins called Regulators of Complement Activation (RCA).

Regulators of Complement Activation control the amplification of the complement cascade. Each of the members of this family share structural characteristics, principally the ~60–65 amino acid Short Consensus Repeat (SCR) modules, which are responsible for complement binding and regulatory functions. Genes encoding the family members are linked and map to chromosome 1q3.2.

The biology of these molecules is of interest in inflammation and homeostasis. However, there is currently a further application for them in the potential use of porcine organs or other organs for grafting to humans. Such xenogenic organs undergo antibody and complement mediated hyperacute rejection.

A limitation to studies of CD46 and other RCAs has been that on transfection with constructs encoding the recombinant proteins in either transient or stable systems very few cells have been transfected and those that are express low amounts of protein. Indeed, in the inventors' laboratory and others, sophisticated cell sorting, cloning and selection procedures have been necessary to isolate appropriate cells. This, in particular, has created problems with the analysis of recombinant CD46, its physiological role and value as a therapeutic agent.

In work leading up to the present invention the inventors have surprisingly found that alterations in a nucleic acid encoding CD46 led to high levels of CD46 production in a transfected eukarotic host. Protein production levels of up to 8 times that obtained from the wildtype gene for CD46 have been observed. These alterations comprised reducing the amount or proportion of adenine (A) and/or thymine (T) in an A and/or T rich region in the nucleic acid.

SUMMARY OF THE INVENTION

The present invention provides a method of increasing or improving mammalian protein production, without demonstrably altering RNA stability, in a host cell where a nucleic acid encoding the mammalian protein has an A and/or T rich region present in an exon, said method comprising altering the nucleic acid by reducing or lowering the amount of A and/or T in said region and transfecting a host cell with said nucleic acid and, under appropriate conditions, obtaining expression of said nucleic acid.

In another aspect the present invention provides a method for enhancing production of RCA proteins in a host cell where a nucleic acid encoding an RCA has an A and/or T rich region present in one or more of its exons said method comprising altering the nucleic acid by lowering the amount of A and/or T in said A and/or T rich region, transfecting a host cell with said nucleic acid and, under appropriate conditions, obtaining expression of said nucleic acid.

In another aspect the present invention relates to a method of increasing production of an RCA protein in a host cell comprising altering a nucleic acid encoding the RCA by deleting a SCR module which contains an AT rich region, or a part thereof, transfecting a host cell with said altered nucleic acid and under appropriate conditions obtaining expression of said nucleic acid.

The present invention also relates to a recombinant nucleic acid construct which is capable of increased production of a mammalian protein in a host cell, without demonstrably altering RNA stability, wherein the amount of A and/or T in one or more A and/or T rich regions present in one or more exons of the nucleic acid construct has been reduced.

The present invention also relates to the proteins produced by the methods of the invention, to proteins encoded by the constructs of the invention, pharmaceutical compositions, host cells transfected with the constructs and transgenic animals expressing the proteins.

The present invention also relates to a method of producing an altered gene encoding a protein wherein said altered gene is capable of increased production of the protein said method comprising altering a gene with one or more A and/or T rich regions present in one or more exons by reducing or lowering the amount of A and/or T in said regions.

BRIEF DESCRIPTION OF THE FIGURES

FIG. 1. Sequence of CD46 constructs in the mutated SCR2 and SCR3 regions. Numbering of the sequence is based on the cDNA clone pm5.1. (Purcell et al., 1991) and extends from the end of SCR1 at nucleotide 303 (nt303) to the beginning of SCR3 (nt564). SCR junctions are shown. The sequence for the construct wtSCR (equivalent to pm5.1) is shown in full with the corresponding single letter code amino acid sequence given above it. Nucleotides which have been substituted in any of the constructs are underlined. For the subSCR2, subSCR3 and subSCR2+3 constructs the sequence matching wtSCR is shown with a dot (.) and the substituted nucleotide is indicated. The deletion mutant construct is as for the other constructs except that the SCR2 deletion is indicated by blanks. The wild type SCR amino acid sequence corresponds to SEQ ID NO:6. The wild type SCR nucleotide sequence corresponds to positions 280–531 of SEQ ID NO:1. The subSCR2 nucleotide sequence corresponds to positions 280–531 of SEQ ID NO:2. The subSCR3 nucleotide sequence corresponds to positions 280–531 of SEQ ID NO:3. The subSCR2+3 nucleotide sequence corresponds to positions 280–531 of SEQ ID NO:4. The deISCR2/subSCR3 nucleotide sequence corresponds to positions 280–342 of SEQ ID NO:5.

Figure 2A:
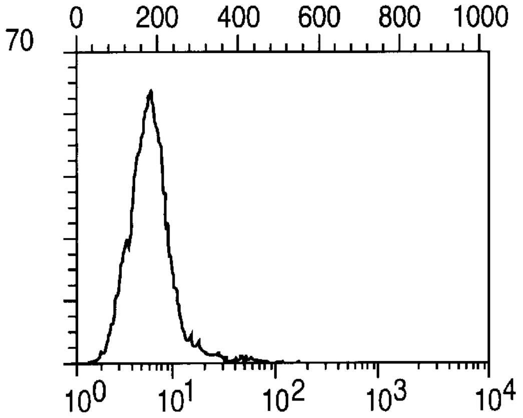
FIG. 2A–2E. Flow cytometry of COS cells after transient transfection with wildtype and mutant constructs. Flow cytometry was performed as described in Materials and Methods. All cells were stained with CD46 mAb E4.3. Panel A shows mock transfected COS cells. Panel B shows profiles for wtSCR transfected cells (---) overlayed with subSCR2 transfected cells (——); panel C shows wtSCR(---) overlayed with subSCR3 (——) panel D shows wtSCR (---) overlayed with subSCR2+3 (——); panel E shows wtSCF (---) overlayed with delSCR2/subSCR3(——). The mutated constructs generated a profile shifted to the right in each case.
Figure 2B:
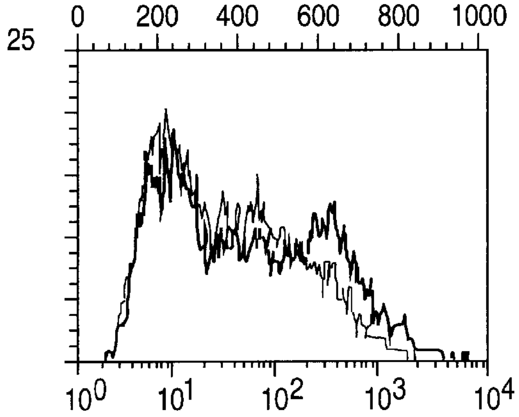
Figure 2C:
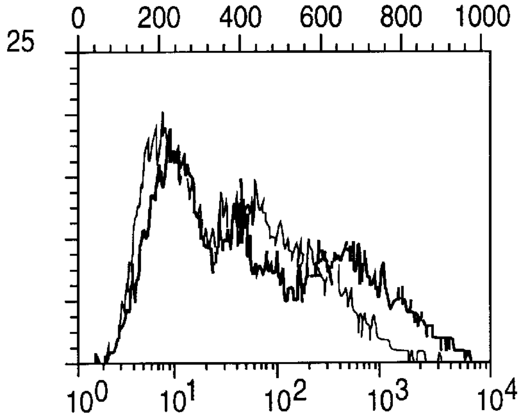
Figure 2D:
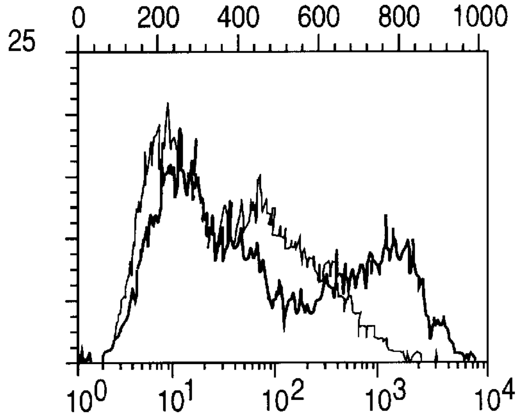
Figure 2E:
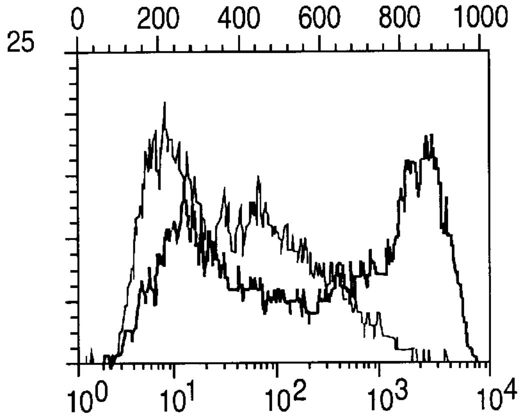

| Summary of Sequence listings | |
|---|---|
| Seq ID No.1 | The cDNA sequence of wtSCR showing amino acid translation |
| Seq ID No.2 | The cDNA sequence of subSCR2 showing amino acid translation |
| Seq ID No.3 | The cDNA sequence of subSCR3 showing amino acid translation |
| Seq ID No.4 | The cDNA sequence of subSCR2 + 3 showing amino acid translation |
| Seq ID No.5 | The cDNA sequence of delSCR2subSCR3 showing amino acid translation |

DETAILED DESCRIPTION OF PREFERRED EMBODIMENTS

In a first aspect the present invention provides a method of increasing or improving protein production in a host cell where a nucleic acid encoding the protein has an A and/or T rich region present in an exon, said method comprising altering the nucleic acid by reducing or lowering the amount of A and/or T in said region, transfecting a host cell with said nucleic acid and, under appropriate conditions, obtaining expression of said nucleic acid.

The phrase "increasing or improving protein production" refers to causing higher production of the desired protein than would routinely be expected in an host cell and includes enhancing protein production. The method of the present invention is particularly directed to providing greater protein production levels where production levels are less than optimal but is not limited to this situation.

The term "host cell" means any cell capable of expressing the nucleic acid encoding the protein. Both prokaryotic and eukaryotic host cells are contemplated.

The term "nucleic acid encoding a protein" refers to a nucleic acid comprising DNA or RNA and includes genes containing introns and exons and cDNA molecules. The term also includes nucleic acids comprising or containing synthetic purine and pyrimidine bases.

The phrase "A and/or T rich region" denotes a stretch of nucleotides which ontains a higher than average amount of A and/or T, and may alternatively be referred to as an "AT rich region". This means a stretch of nucleotides with a greater than average AT content for the particular species from which the nucleic acid is derived. For instance an AT rich region in a nucleic acid encoding a human protein would be a region that contains more than 60% A and/or T in a particular span of nucleotide sequence. It should be understood that the term AT rich region includes an AU rich region (where RNA is the nucleic acid) and that "A and/or T" also means "A and/or U" in an RNA context.

The term "exon" means that part of a nucleic acid actually encoding the protein.

The phrase "altering the nucleic acid by reducing or lowering the amount of A and/or T, in said region" means that A and/or T nucleotides in the AT rich region are replaced by substitution of other bases (such as G or C, or synthetic nucleotides) or that these nucleotides are deleted and not replaced by another base. Usually such a deletion will be an "in frame" deletion thus not producing a frame-shift. The reduction or lowering the amount of A and/or T includes reference to lowering the proportion of A and/or T with respect to G and/or C nucleotides. The term "mutation" is also used to refer to such alterations throughout the specification.

Where the nucleotides are replaced by other bases the resultant alteration may be silent so that the codon encodes the same amino acid. Silent mutations are well known to those skilled in the art and most commonly involve changing the third nucleotide of the codon.

Alternatively, the replacement may be conservative, i.e. results in a codon specific for an amino acid with similar properties to the original amino acid specified. Suitable conservative amino acid substitutions are given in Table A below. Those skilled in the art will know which bases to substitute to confer a conservative amino acid substitution Typical substitutions are those made in accordance with Table A.

TABLE A

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Ala |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Alternatively an entirely different codon may be created by insertion of a nucleotide other than A or T depending on the protein product desired. It will be understood that this will usually be an in frame insertion.

The term "transfecting" means causing the nucleic acid to be taken up by the cell. The nucleic acid will usually be present as a component of an expression vector or the like. The resultant transfection may be transient, where the gene is maintained on an episome, or stable. Stable transfection is achieved where the gene is integrated into the cell genome and becomes stably heritable. Nucleic acids can also be introduced into host cells via viral vectors by infection of host cells with, for example, recombinant vaccinia or adenoviruses.

The method of the invention contemplates increasing production of all proteins encoded by nucleic acids with AT rich regions in their exons where it is desired to produce the proteins in an eukaryotic system. The nucleic acids encoding candidate proteins may be screened for AT rich regions in their exons by standard techniques such as searching the GenBank data base. These nucleic acids include those encoding cell surface proteins, peptide hormones, cytokines, growth factors, receptors and their ligands, novel recombinant proteins for therapeutic uses or reagents where it is desired to increase production of the protein. Complement regulating proteins, particularly those containing short consensus repeat domains, such as CD46, are of particular interest.

The prokaryotic cell used in the method may by any prokaryotic cell suitable for expressing the required gene. This includes *Escherichia coli* (for example *E. coli* MC1061, *E. coli* DH5$_\alpha$, *E. coli* NM522, EK12 and *E. coli* W3110), bacilli such as *Bacillus subtilis* or other enterobacteriaciae such as, for example, *Salmonella typhimurium* or *Serratia marcesans* and various Pseudomonas species. Preferably non-pathogenic, attenuated strains of these organisms are used.

The eukaryotic cell used in the method may be any eukaryotic cell suitable for expression of the required gene. Suitable cells which will be known by those skilled in the art, include animal cells such as COS-7, CHO-K1, WOP-3027, C127, VERO, HeLa, W138, BHK, 293, MDCK and L929. Others such as Saccharomyces, Kluyveromyces, *Pichia pastoris*, Schwanniomyces and Hansenula may also be suitable.

Suitable vectors used to transfect the host cell with the nucleic acid in the method will be well known to those skilled in the art. Suitable prokaryotic vectors include pGEX, pKC30, pKK173-3, pET-3 and others. These vectors will preferably contain replicon and control sequences that are compatible with the chosen host cell described above. For example, in mammalian cells the control functions on eukaryotic expression vectors are usually provided by viral sources such as Adenovirus 2, polyoma, HIV-1, human cytomegalovirus and SV40.

The phrase "under appropriate conditions" means conditions suitable to obtain expression of the nucleic acid and production of the protein. Culture conditions such as nutrients, temperature and so on will be well known to those skilled in the art.

There appears to be a number of possible mechanistic explanations for the increased level of protein production provided by lowering the A and/or T content of the AT rich regions present in an exon. Examples include improved stability of transcripts, increased delivery of mRNA to the cytoplasm, increased efficiency of translation by ribosomes, increased translation due to mRNA superstructure or in fact a combination of two or more of these factors. Without wishing to be bound by theory it appears likely that the increased protein production can be explained by an increased rate of protein translation. Data indicating that the increased protein production is limited to intact cells and is not evidenced in cell-free translation systems tends to indicate the effect is due to some interaction between mRNA transcripts, ribosomes, polysomes, RNA-binding proteins and/or other factors such as sequence-dependent 3-dimensional mRNA structure rather than substrate availability (such as for example RNA stability effects) or simple structural effects or simple protein translation component interaction.

While there is still some speculation about the exact mechanism responsible for the improved protein production associated with the present invention, it is nontheless noted that protein production increases of up to or exceeding 20-fold in terms of cell-surface molecule expression can be obtained. The increased protein production appears to be most pronounced, especially in the case of CD46 translation, when the reduction in A and/or T content is effected within a region up to about 540 bases from the initiation codon.

In a preferred embodiment the host cell used in the method is a eukaryotic cell. This is because it is often desirable to obtain post-translational modifications of the recombinant protein, such as glycosylation which cannot always be provided by prokaryotic hosts and some insect cells.

In another preferred embodiment the nucleic acid encodes an RCA which has an A and/or T rich region in one or more of its exons. The RCA may be CD46, CD55, CD35 or factor H amongst others.

In a particularly preferred embodiment the present invention relates to a method of increasing or improving CD46 production in a eukaryotic cell where the gene encoding CD46 is altered by reducing or lowering the amount of A and/or T in an A and T rich region in one or more exons of said gene and transfecting a eukaryotic cell with said altered gene and, under appropriate conditions, obtaining expression of said gene.

The term "CD46" used herein refers to all native isoforms and recombinant splice variants, including native forms not commonly expressed by human cells.

Any CD46 gene natural or recombinant may be used as a starting point for synthesis of the altered CD46 gene. This includes the native CD46 genes and the CD46 constructs disclosed in PCT/AU91/00199 (the specification of which is herein incorporated by reference). cDNA CD46 constructs which by definition comprise exons are preferred. In the Examples herein clone pm5.1 of PCT/AU91/00199 is used as a starting point.

In a particularly preferred aspect of the invention the alterations are made to AT rich regions encoding the short consensus repeat (SCR) domains or to putative polyadenylation signals. This is particularly so when putative polyadenylation signals occur inappropriately within protein-coding exons. More particularly preferred are alterations to the boundary or junction, surrounding the 3rd and 4th exons in CD46 cDNA constructs. The 3rd and 4th exons encode one of the SCRs and contains a stretch of 49 nucleotides 78% which are A or T which may be altered. In addition, alterations to a smaller A rich region within the adjacent exon 5 may also be carried out separately or in conjunction with the above alterations.

Although exons 3, 4 and 5 have been the target for the alterations so far described other regions of the CD46 gene may be contemplated such as exons 6 and 14.

The alteration may be made by replacing the A or T nucleotides with other bases or deleting the A or T nucleotides and not replacing them with other bases as described above. The substitutions will depend on the structure of the protein required and may be silent or conservative.

Still more preferably the AT content of the region between nucleotides 406 to 454 of FIG. 1 is reduced from 78% to approximately 60%, more preferably approximately 55%.

Alternatively, still more preferably the A rich region in SCR3 is reduced, which interrupts a putative poly A signal on the wildtype CD46 gene, and the nucleotides substituted extend 5' to the end of the region encoding SCR2.

Alternatively more preferably the SCR2 is deleted and optionally there are substitutions in the SCR3.

In addition to the above alteration mutations can also be made which render the CD46 protein soluble. Preferably a stop codon is created for example at position 1022 of pm5.1 (Purcell et al (1991)) by changing an A to a G.

In a still more preferred form the invention relates to a method of using the constructs of subSCR2, subSCR3, subSCR2/3 and delSCR2/subSCR3 as illustrated in FIG. 1. By way of explanation a construct containing substitutions in exons 3 and 4 are denoted subSCR2, substitutions in exon 5 is denoted subSCR3 and substitutions in exons 3, 4 and 5 are denoted subSCR2+3. The construct which comprises deletion of SCR2 and contains a substitution in SCR3 is designated delSCR2/subSCR3.

Where substitution of A or T nucleotides is desired splice overlap extension (SOE-PCR) may be used. Other methods such as PCR based mutagenesis, and ligation of an appropriately mutated synthetic nucleotide will be known to persons skilled in the art. Deletion of A or T nucleotides or stretches of nucleotides may be carried out by standard site directed mutagenic techniques.

Preferably the initial constructs containing the altered CD46 cDNA are made in bacterial vectors. Once it has been confirmed that the desired construct has been produced then the altered CD46 gene may be ligated into a eukaryotic vector such as pcDNA1, pCDM8, PGK-neo, pEE6.hCMV.GS, pHIV, pHMG or pMJ601 and others.

The desired construct containing the altered gene is then used to transfect an appropriate host cell. Preferably this is a eukaryotic host cell. Standard transfection techniques may be employed preferably using Lipofectamine (Gibco-BRL, Gaithersburg, USA) or a similar reagent. COS-7 or CHO-K1 cells are preferably transfected although other eukaryotic cells may be utilised such as WPO-3027, L929 and so on.

In a related aspect the present invention provides a method for enhancing production of RCA proteins in a host cell where a nucleic acid encoding an RCA has A and/or T rich regions present in one or more of its SCR modules, said method comprising altering the nucleic acid by lowering the amount of A and/or T in said A and/or T rich regions, transfecting a host cell with said nucleic acid and, under appropriate condition obtaining expression of said nucleic acid.

The terms "A and/or T rich region" and "lowering the amount of A and/or T" have the same meaning as given above.

Preferably a eukaryotic host cell is used in the method such as those described above.

More preferably the AT rich regions in SCR2 and SCR3 are subject to alteration.

The above method is based on the observation that alterations in nucleotides encoding the SCR2 and SCR3 modules in CD46 produce an additive effect which greatly increases the amount of protein produced.

Preferably the nucleic acid encodes CD46.

Preferably the alteration is obtained through silent nucleotide substitutions.

More preferably the nucleic acid is the construct subSCR2+3 described herein.

In a second aspect the present invention relates to a method of increasing production of an RCA protein in a host cell comprising altering a nucleic acid encoding the RCA by deleting one or more SCR modules with contains an AT rich region, or a part thereof, transfecting a host cell with said altered nucleic acid and under appropriate conditions obtaining expression of said nucleic acid.

Preferably a eukaryotic host cell, such as those described above is employed in the method.

Optionally, in the above method other parts of the nucleic acid, including AT rich regions outside of the SCR module (s) may also be changed such as by reducing the amount of A and/or T in the AT rich region.

Preferably the altered nucleic acid encodes a CD46 isoform. More preferably the nucleic acid encoding CD46 is delSCR2/subSCR3 described herein.

In a third aspect the present invention also relates to a recombinant nucleic acid construct which is capable of increased production of a protein in a host cell wherein the amount of A and/or T in one or more A and/or T rich regions present in one or more of the exons has been reduced.

The term "recombinant nucleic acid construct" refers to a molecule made up of nucleic acids which have been combined from different sources and is capable of transfecting a host cell.

The term "increased production" refers to expression levels higher than that demonstrated in previous constructs including those containing native genes encoding the protein of interest.

The terms "A and/or T rich region", "exon", "host cell" and reduction of the amount of the A and/or T in the A and/or T rich region have the same meanings as given earlier.

Such constructs may be produced by the methods given earlier.

Preferably the host cell is a eukaryotic host cell.

Preferably the constructs comprise nucleic acids which encode proteins, the genes of which in their native state contain A and/or T rich regions in their exons. The nucleic acids may encode proteins such as cell surface proteins, peptide hormones, growth factors, receptors and their ligand, novel recombinant proteins for therapeutic uses or reagents. Complement regulating proteins, particularly those containing short consensus repeat domains are included.

In a particularly preferred aspect of the invention the constructs encode an altered CD46 cDNA sequence. While any CD46 cDNA may be used as a starting point those disclosed in PCT/AU91/00199 (which is incorporated herein by reference), particularly clone pm5.1 are preferred.

In a more preferred aspect the construct comprises alterations in one or more of the following AT rich regions of FIG. 1 of the CD46 construct, or its equivalent nucleotides 406 to 454, 504 to 516 and 530 to 561.

In a preferred aspect of the invention the CD46 constructs of the invention have been altered so that the proportion or amount of A and/or T in the AT rich regions of the SCR domains has been reduced and optionally the putative poly A signal have been removed.

In a more preferred aspect of the present invention the construct comprises alterations which have reduced the amount of A and/or T in the AT rich region of the boundary or junction surrounding the 3rd and 4th exons.

Still more preferred is a construction comprising a reduction of A and/or T in the 49 nucleotide stretch 78% of which comprises A and/or T in the 3rd and 4th exons or a reduction in the A rich region within the adjacent exon 5.

In a most preferred aspect the invention relates to the constructs subSCR2, subSCR3, subSCR2+3 and delSCR2/subSCR3.

The above constructs or their derivatives which result in production of CD46 at the cell surface may be used to produce transgenic animals such as transgenic pigs whose organs produce cell surface CD46. Such organs may be used in transplantation therapy. The term "derivative" above means recombinant constructs containing the altered CD46 gene or gene segments derived from the above constructs.

The present invention also relates to a purified preparation of a protein produced by the first and second aspects of the invention and to a purified preparation of a protein encoded by the constructs of the third aspect of the invention.

The term "purified preparation" refers to preparation of proteins separated from, in at least some degree, the proteins and other constituents of the host cell. Preferably the protein is at least 50% pure, preferably 60% pure, more preferably 70% pure, still more preferably 80% pure and still more preferably 90% pure, or more, when compared to other proteins or constituents as determined by weight, activity, amino acid similarly antibody reactivity or other convenient means.

Preferably the protein is CD46BC1. Most preferably the invention relates to a soluble CD46 (sCD46(BC)) protein encoded by sol-subSCR3 (see Table 1) as described or an equivalent.

The invention also relates to host cells expressing the desired protein made in accordance with the first and second aspects of the invention or transformed with the constructs of the third aspect of the invention.

In a particularly preferred aspect the invention relates to stably transfected host cells or transgenic animals expressing the desired protein.

The invention also relates to a method of producing an altered gene encoding a protein wherein said altered gene is capable of causing increased production of the protein said method comprising altering a gene with one or more A and/or T rich regions present in one or more exons by reducing or lowering the amount to A or T in said regions.

The terms, phrases and methods for producing the altered gene used above have been explained earlier.

Preferably the altered gene is capable of causing increased production of a protein in a eukaryotic host cell.

Preferably the altered gene comprises a CD46 encoding segment.

Preferably the primers described in Table 1 are used in splice overlap extension PCR to produce the altered CD46 gene.

In another aspect the present invention comprises a pharmaceutical composition comprising as an active ingredient a purified protein preparation described above together with a pharmaceutically appropriate carrier or diluent.

The pharmaceutical composition may be used in the treatment of diseases for which the active ingredient is indicated. In the case where the active ingredient is CD46 then the composition may be used to prevent complement mediated, or inflammation mediated tissue damage, to enhance immunity to tumours and viruses, to control the process of fertilization, to prevent recurrent spontaneous abortion of the foetus during pregnancy and to facilitate engrafling of transplanted tissue as previously described in PCT/AU91/00199 which is incorporated herein by reference.

The formation of pharmaceutical compositions is generally known in the art and reference can conveniently be made to Remington's Pharmaceutical Sciences, 17th ed, Mack Publishing Co, Pennsylvania, USA.

In a preferred aspect the present invention comprises a pharmaceutical composition comprising CD46 made according to the above methods or derivable from the above constructs together with a pharmaceutically appropriate carrier or diluent.

In a particularly preferred aspect the present invention comprises a pharmaceutical composition comprising the soluble CD46 protein as herein described.

The invention will be further described with reference to the following non-limiting examples.

EXAMPLE 1

Materials and Methods

The CD46 Isoform Nomenclature

The CD46 gene produces 4 commonly expressed mRNAs (up to 14 in total) by alternative RNA splicing (Russell et al., 1992). To simplify representation of CD46 protein isoforms only the variably spliced regions, the STP-A,B,C segments (encoded by exons 7, 8 and 9) and cytoplasmic tails (tail 1 is encoded by exon 13, whereas tail 2 is encoded by exon 14 after the splicing out of exon 13) are denoted unless mutated for the purposes of the present application. The term "mutated" used here means the same as the alterations discussed earlier. The wildtype protein isoform produced in this application includes STPs B and C (exons 8, 9) and cytoplasmic tail 1 (exon 13) and is denoted by CD46(BC1) (the equivalent protein is encoded by pm5.1 cDNA in Purcell et al, 1991 and PCT/AU91/00199). The protein isoform containing STPs B and C and cytoplasmic tail 2 is denoted by CD46(BC2). The soluble protein produced here is referred to as sCD46(BC), because the stop codon is at the predicted transmembrane boundary.

Nucleotide substituted constructs and products are designated by the protein domain encoded by the targeted exons. Thus the construct containing substitutions in exons 3 and 4 is subSCR2; substitution to exon 5 is subSCR3; and substitutions to exons 3, 4 and 5 is subSCR2+3. The construct which encodes an SCR2 deletion and contains SCR3 substitutions is designated delSCR2/subSCR3.

Mutagenesis of CD46 cDNA

Silent nucleotide substitution was achieved using Splice Overlap Extension PCR (SOE-PCR) (Horton et al., 1988). Firstly, two PCR reactions amplified two overlapping DNA fragments which contained the required mutations in complementary sequences at one end and EcoRI sites at the other end. Secondly, the two fragments were spliced together in a SOE-PCR reaction using the primers containing the EcoRI sites. The PCR primers and the nucleotide positions to which they annealed are shown in Table 1A. The overlapping DNA fragments containing mutations were produced in two PCR reactions using the templates and oligonucleotide combinations shown in Table 1B.

The products of the first two PCR reactions for each mutant, the 5' and 3' PCR fragments, were isolated after electrophoresis in low-melt agarose (Nusieve), diluted and used directly as template for the SOE-PCR reactions. All the SOE-PCR reactions, including the unrutated wildtype CD46, used On232 and On241 as oligonucleotides. The PCR and SOE reactions were performed in a DNA Thermal Cycler (Perkin Elmer Cetus) using Amplitaq enzyme and buffer (Perkin Elmer Cetus). The cycle conditions for the first two PCR were 3 cycles of 2 min at 94° C., 1 min at 50° C. and 1 min at 72° C. followed by 22 cycles of 30 sec at 94° C., 1 min at 60° C. and 1 min at 72° C. The SOE-PCR cycle conditions were 3 cycles of 2 min at 94° C., 1 min at 44° C. and 2 min at 72° C., followed by 22 cycles of 30 sec at 94° C., 1 min at 60° C. and 2 min at 72° C.

While not wishing to be bound by theory the above mutations appear to restore the usual AT/GC balance (proportion of AT:GC) found in marnmalian nucleic acids and this restoration of balance appears to result in increased protein production.

Mutant DNA Constructs and Expression Vectors

PCR products were end-filled with DNA polymerase (Klenow fragment) (Boehringer Mannheim) and phosphorylated with T4 polynucleotide kinase (New England Biolabs). The DNA was purified after agarose gel electrophoresis using NA45 paper (DEAE)(Schleicher and Schuell) followed by MagicPrep DNA clean-up system (Promega Corp.). The DNA products were ligated (DNA ligase, New England Biolabs) into the Sma I site of pBluescript II SK (Stratagene) and transformed into XL1 Blue *E. coli* (Stratagene). Plasmid DNA was prepared of clones containing mutations using Maxiprep (Promega Corp.) and the entire sequence was confirmed by dideoxy sequencing using a Sequenase™ kit (United States Biochemical Corp.). All products contained the nucleotide mutations without PCR error. The DNA inserts were released from the pBluescript vector by digestion with EcoRI, end-filled with DNA polymerase (Klenow fragment) (Boehringer Mannheim), ligated into the Eco RV site of pcDNA I (Invitrogen Corp.) and transformed into MC1061/p3 *E. coli*. The cloning sites were confirmed by dideoxy sequencing. Plasmid DNA for transfection was prepared using Wizard™ Maxiprep DNA purification system (Promega Corp).

Transfection

COS-7 green monkey fibroblasts and CHO-K1 Chinese hamster ovary fibroblasts were cultured in DMEM medium supplemented with 20 $\mu$g/ml glutamine, 100 U/ml penicillin, 100 $\mu$g/ml streptomycin, and 10% v/v foetal bovine serum (CHO-K1 medium also contained 20 $\mu$g/ml proline, 14 $\mu$g/ml hypoxanthine and 3.9 $\mu$g/ml thymidine), in a humidified 10% $CO_2$ atmosphere.

Plasmid DNA (pcDNA1-CD46 constructs) was introduced into cultured cell lines with Lipofectamine (Gibco-BRL) in serum-free and antibiotic-free DMEM medium, according to the manufacturer's instructions. One six-well plate of COS-7 cells was transfected with each construct. The cells transfected with cell-surface CD46(BC1) were harvested 48 hours after transfection and were split into aliquots to be analysed by Southern, Northern and Western blotting, radioimmunoassay (RIA) of cell lysates, fluorescent microscopy and flow cytometry. For the expression of soluble CD46 constructs, the COS-7 cells were cultured in serum-free medium which was collected 120 or 148 hours after transfection. For generation of transfected CHO-K1 cells with stable construct integration, PGK-neo plasmid (a gift from Dr Richard Harvey, WEHI, Melbourne, Australia) was cotransfected, with a 10-fold excess molar concentration of the pcDNA1-CD46 construct plasmid DNA. Transfected CHO cells were selected for stable expressors with 1.2 mg/ml G418 and assayed for cell surface expression of CD46 after two or more weeks.

Analysis of Cell Surface CD46(BC1) Production by Immunofluorescence

CD46 protein processed on the plasma membrane, or as intracellular protein in permeabilised cells, was assayed by two-stage immunofluoresence labelling. The primary anti-CD46 mAb (E4.3 IgG2a, Sparrow & McKenzie 1983; or M177 IgGI, Seya et al, 1990) or isotype control mAb (MEM-43 IgG2a anti-CD59, Stefanova et al, 1989) was incubated with cells for more than 30 min on ice, cells were washed and FITC sheep(Fab)-anti-mouse Ig (Silenus, Melbourne, Australia) was added for a further 30 min on ice.

Fluorescence was assessed by flow cytometry (FACScan II, Becton Dickinson) of cell suspensions or by microscopy of near-confluent cell monolayers.

Analyses of CD46(BC1) in Whole Cell Lysates

Whole cell lysates were prepared as described at a concentration of $5\times10^6$ cells/ml. An equivalent number of cells was used for all samples and Western blotting was performed as described (Laemmli, 1970). The proteins present in the lysate were separated by non-reducing SDS-PAGE, blotted and probed with the mAb E4.3. The capture/tracer RIA used mAb E4.3 to capture the CD46 protein and $^{125}$I-labelled M177 (a gift from Seya) as the tracer and was performed as described, but with approximately 10000 cpm input counts of the tracer (Johnstone et al., 1993).

Analyses of DNA and RNA

RNA was prepared using a modification of the procedure of Chirgwin et al. (1979). Northern blotting was performed as described (Milland et al., 1990) except that the membrane was Hybond-N (Amersham) and the transfer was by gravity in a downwards direction. Cellular DNA was prepared and Southern blotting was performec as described (Southern) using Hybond-N$^+$ (Amersham) as the membrane. For the Northerns and Southerns the probe used for hybridisation was pm5.1 cDNA (Purcell et al, 1991), labelled using the Megaprime DNA Labelling System (Amersham).

Plasmid Constructs

The sequences of the SCR mutation are shown in FIG. 1. All the final constructs were in the pcDNA1 vector and had the same cloning sites derived from the oligonucleotides used for the PCR. The construct containing unrmutated (wtSCR) sequence is derived from the original pm5.1 cDNA clone (Purcell et al., 1991). This and each of the silent substitution constructs discussed below encodes wildtype CD46(BC1) protein. The subSCR2 construct contains silent nucleotide substitutions in the region in SCR2 around the exon 3/4 splice site and encodes wildtype CD46(BC1) protein. The substitutions reduce the A/T content of the region between the nucleotides 406 and 454 from 78% to 55%. The subSCR3 construct contains silent nucleotide substitutions to an A-rich region in SCR3 (including one substitution at the end of SCR2) and also interrupts a putative polyadenylation signal and encodes wildtype CD46 (BC1) protein. The subSCR2+3 construct contains a combination of the SCR2 and SCR3 changes and encodes wildtype CD46(BC1) protein. The final cell surface construct, delSCR2/subSCR3, has SCR2 deleted and substitutions to SCR3. This construct encodes a mutant protein without SCR2, called CD46(delSCR2/BC1). Two DNA constructs were mutated to encode a soluble protein called sCD46(BC). The first construct, sol-wtSCR was produced by the substitution of an A for a G at nucleotide 1022 to produce a stop codon before the transmembrane domain. The sol-subSCR3 construct contains the stop codon mutation and the silent nucleotide substitutions in SCR3 described above.

Silent Nucleotide Substitution Increases the Production of Cell Surface CD46(BC1)

Initially the inventors showed that mutation increased protein production CD46 by photomicrography. In these experiments cells were transfected in wells and stained with E4.3. Results are not shown. The order of increasing protein production was wtSCR, subSCR2, subSCR3, subSCR2+3 and delSCR2/subSCR3. The improvement in CD46 production was also observed after transfection of WOP-3027 cells (data not shown).

Flow cytometry showed that more COS-7 cells were producing CD46 on their surface and that the cells were also producing at a significantly higher level after transfection with the mutated constructs compared to the wtSCR construct (FIG. 2). The improvement in production was in the same order as for the photomicrography. As would be expected, a proportion of the cell population has a similar fluorescence to the mock transfected cells and represent untransfected or transfected cells without cell surface CD46, however, in panels C, D and E, it appears that all cells exposed to the mutated constructs were transfected and expressed CD46: the entire profile in each case is shifted to the right in comparison to the profile of wildtype transfected cells.

Figure 3:
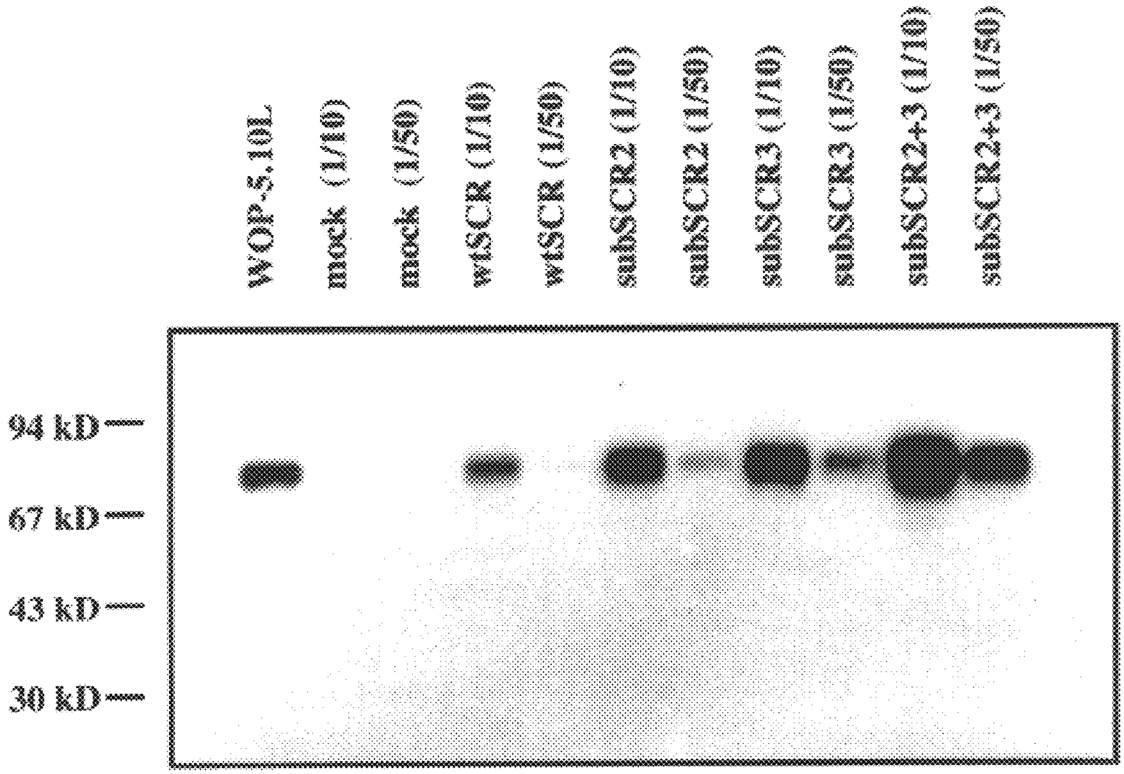
FIG. 3. Western blot analysis of COS cell lysates transfected with CD46 constructs (see Materials and Methods). Lanes contain 40 $\mu$l of a dilution of cell lysate at $5\times10^6$ cells per ml. From left to right lanes contain transfectant WOP-5.10L (CD46 BC2) at 1/5 dilution; COS cell lysate transfected with no DNA at 1/10 dilution and 1/50 dilution COS cell lysate transfected with wtSCR2 at 1/10 and 1/50 dilution; COS cell lysat transfected with subSCR2 at 1/10 and 1/50 dilution; COS cell lysate transfected wit subSCR3 at 1/10 and 1/50 dilution; and COS cell lysate transfected with subSCR2+3 at 1/10 and 1/50 dilution. Molecular weight markers are indicated.

Silent Nucleotide Substitution Increases the Production of CD46(BC1) in Cell Lysates Cell lysates were prepared from transfected cells. These lysates include all cel. that were transfected including the large proportion of cells that do not produce significant amounts of cell surface CD46. In all cases, the protein produced after transfection of CD46(BC1) was the expected size (66 kDa) by Western blotting (FIG. 3). There is more CD46 in the lysates from cells transfected with mutated CD46 DNA compared with unmutated CD46 DNA. The order of improvement in production was the same as for cell surface expression and cells transfected with the subSCR2+3 construct gave the best result compared to the wtSCR construct.

Figure 4:
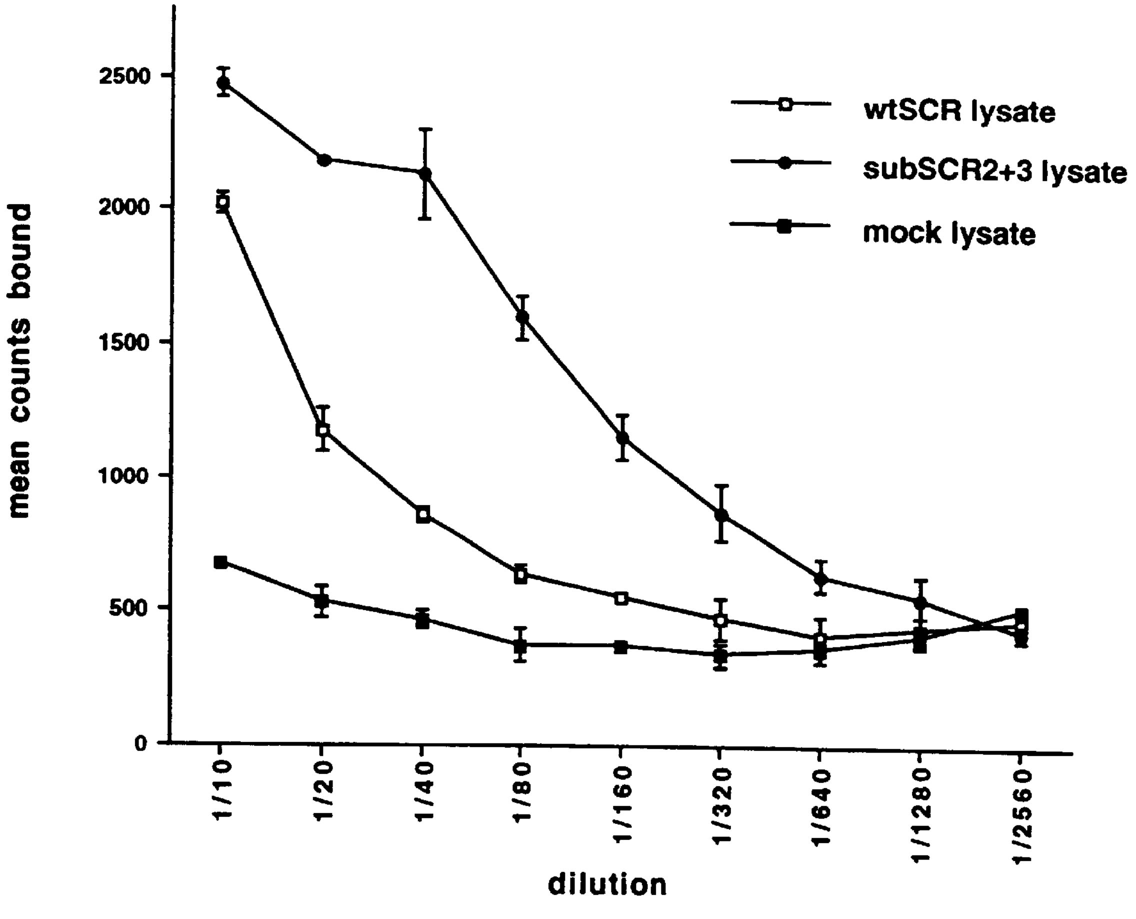
FIG. 4. Semi-quantitative radioimmunoassay (see Materials and Methods) of COS ce lysates. An equivalent number of transfected cells was used for each sample. The mea number of counts bound (duplicates) with standard error is shown against dilution facto; The titration curves are for lysates of mock (■), wtSCR (□) and subSCR2+3 (●) transfected cells.

To enable a better estimate of the difference in the level of CD46 proteins, RIA was performed (FIG. 4). The population of cells transfected with subSCR2 or subSCR3 had approximately twice as much CD46 in their lysates compared to the wtSCR transfected cells. The cells transfected with subSCR2+3 had approximately eight times as much CD46 in their lysates compared to the wtSCR transfected cells. These results suggest that the nucleotide sequences in SCR2 and SCR3 may be interacting in some way, since the silent substitutions to SCR2 and SCR3 appear to improve the level of protein expression in an additive way. There may also be other nucleotide sequences in SCR2 affecting the level of protein expression, since the total deletion of SCR2 increases the level of expression more than the silent nucleotide substitutions of SCR2+3.

Silent Nucleotide Substitution Increases the Production of Soluble CD46(BC)

Figure 5:
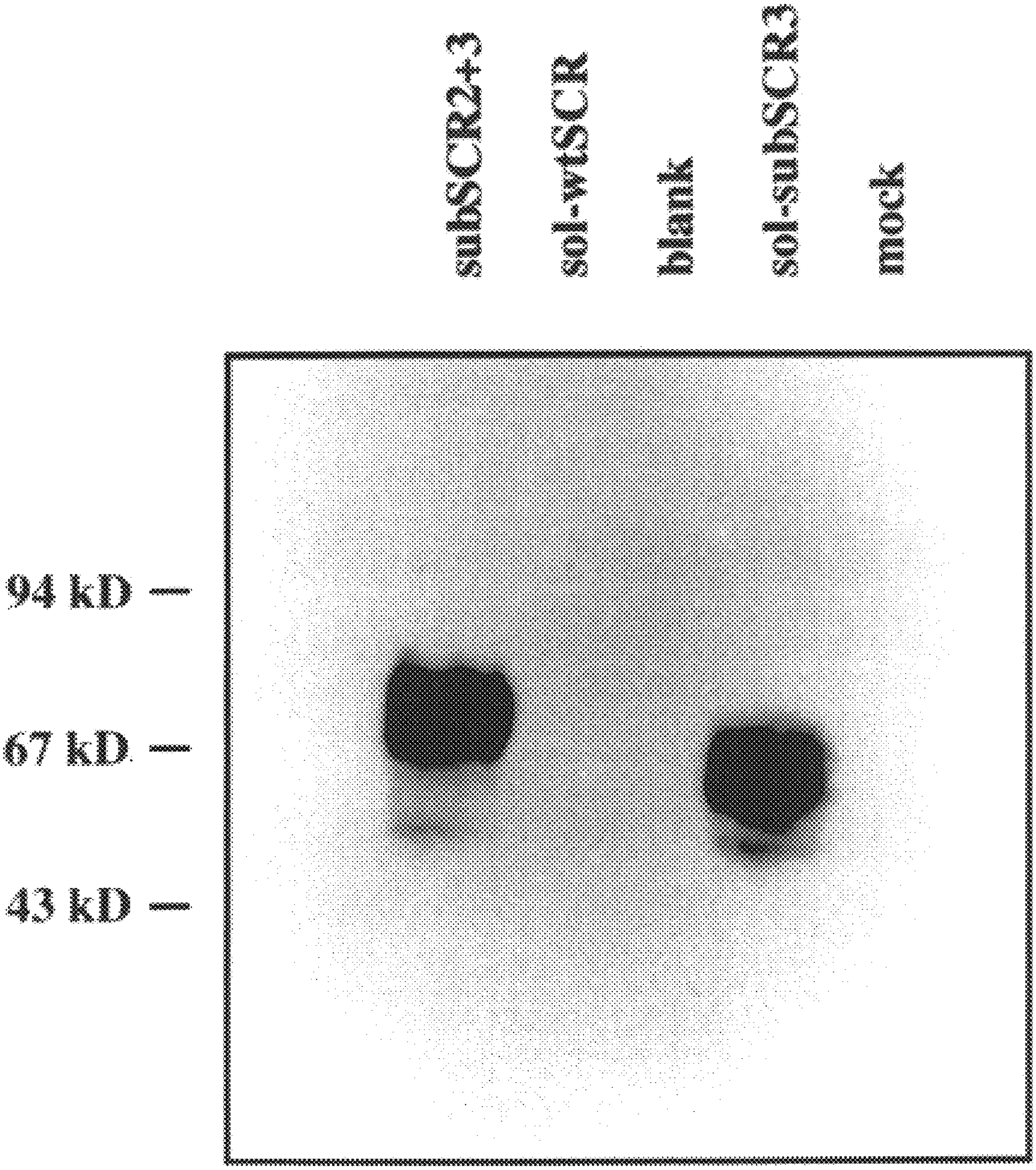
FIG. 5. Western blot analysis of COS cell serum-free supernatant 168 hours aft, transfection with CD46 constructs (see Materials and Methods). Lanes contain 40 $\mu$l undiluted supernatant. From left to right lanes contain supernatant from cells transfecte with the cell surface construct subSCR2+3; the soluble construct sol-wtSCR; blank; tl soluble construct sol-subSCR3; and no DNA (mock). Molecular weight markers a indicated.
Figure 6:
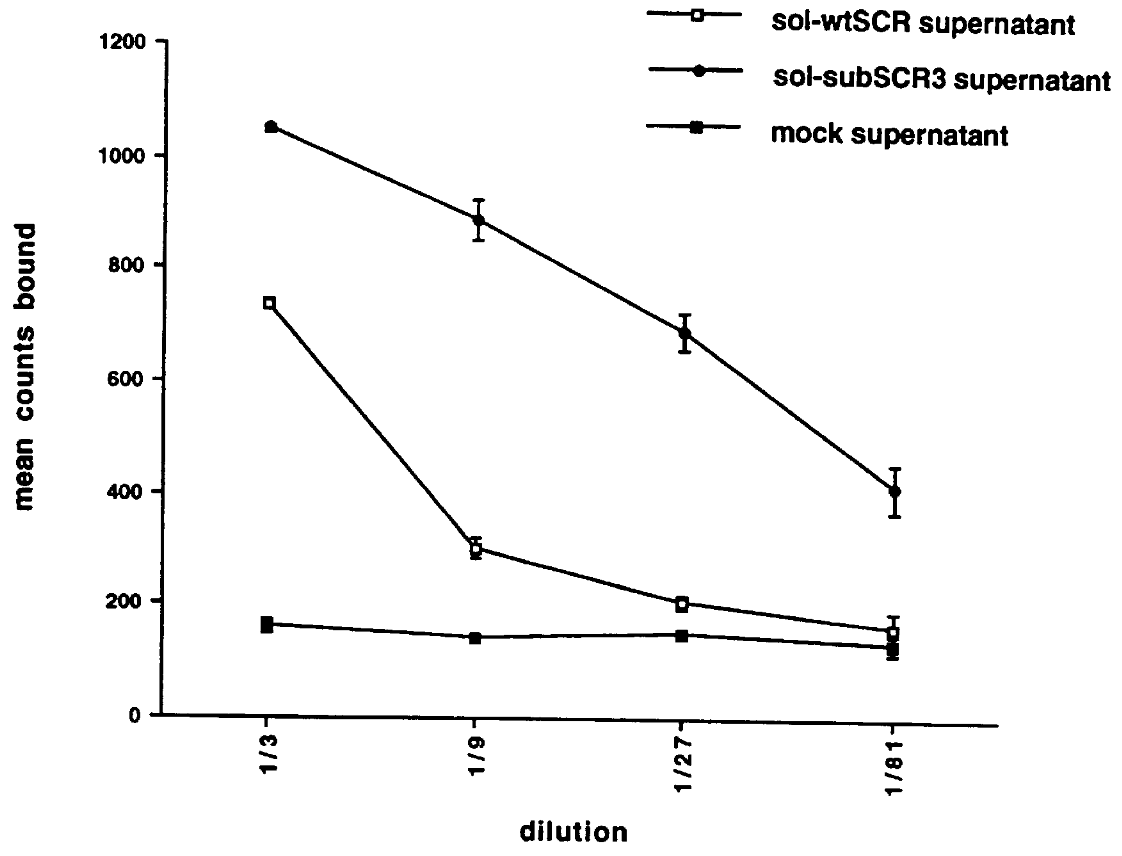
FIG. 6. Semi-quantitative radioimmunoassay (see Materials and Methods) of COS cell supernatants. An equivalent amount of tissue culture supernatant was used for each ample. The mean number of counts bound (duplicates) is shown against the dilution factor. The titration curves are for supernatants of mock (■), sol-wtSCR (□) and sol-subSCR3 (●) transfected cells.

The silent nucleotide substitutions in SCR3 also enabled significantly greater quantities of sCD46(BC) to be expressed in a transient COS system. The sol-subSCR3 construct produced protein detectable by Western blotting in the serum-free supernatant of cells 148 hours after transfection of COS-7 cells (FIG. 5). Supernatant from similarly transfected cells 120 hours post-transfection was analysed by RIA. The level of soluble material secreted by cells transfected with sol-subSCR3 was approximately nine times that of cells transfected with sol-wtSCR (FIG. 6). COS cells transfected with the subSCR2+3 (shown in FIG. 5) or delSCR2/subSCR3 (data not shown) also shed or secreted significant amounts of CD46 protein into the tissue culture supernatant which was in addition to CD46 expressed on the cell surface. None of the other cell surface transfectants produced detectable quantities of CD46 in the supernatant.

Figure 7:
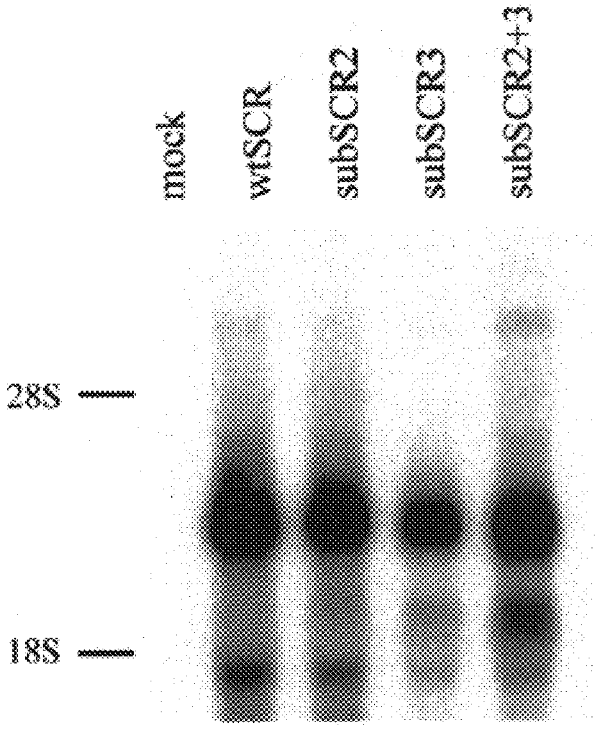
FIG. 7. Northern blot analysis of CD46 mRNA in transfected COS cells. Total RNA prepared from COS cells 48 hours after transfection was separated by electrophoresis (10 $\mu$g/track). Northern blotting was as described in Materials and Methods. The position of the 28S and 18S ribosomal RNA bands are indicated. Lanes 1–5 contain RNA prepared from COS cells transfected with no DNA, wtSCR, subSCR2, subSCR3 and subSCR2+3, respectively.
Figure 8:
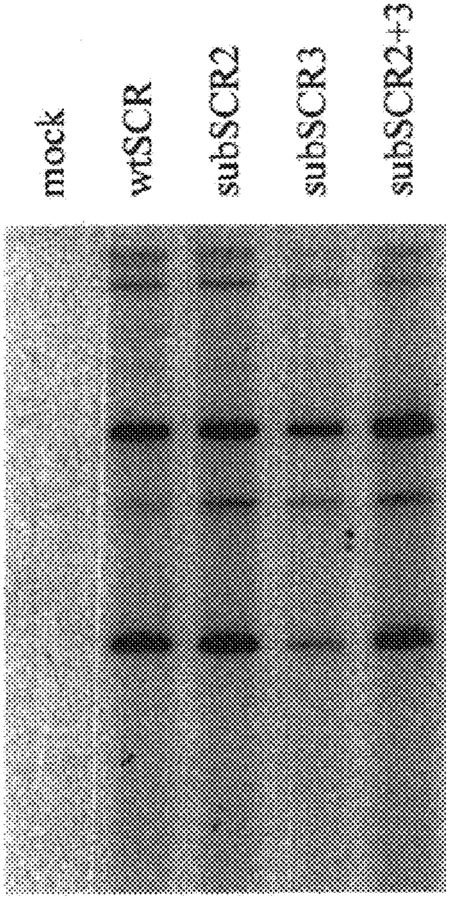
FIG. 8. Southern blot analysis of CD46 mRNA in transfected COS cells. DNA prepared from COS cells 48 hours after transfection was separated by electrophoresis (5 $\mu$g/track). Southern blotting was as described in Materials and Methods. Lanes 1–5 contain DNA prepared from COS cells transfected with no DNA, wtSCR, subSCR2, subSCR3 and subSCR2+3, respectively.
Figure 9A:
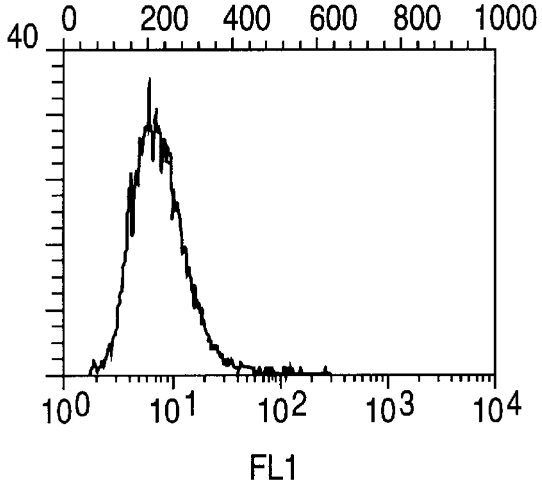
FIG. 9A–9D. Flow cytometry of CHO cells after stable transfection with wildtype and mutant constructs. Flow cytometry was performed as described in Materials and Methods. All cells were stained with CD46 mAb E4.3. Panel A shows pgk-neo transfected CHO cells. Panel B shows profiles for wtSCR transfected cells (-----) overlayed with subSCR2 transfected cells (——); panel C shows wtSCR (---) overlayed with subSCR3 (——); panel D shows wtSCR (---) overlayed with subSCR2+3 (——).
Figure 9B:
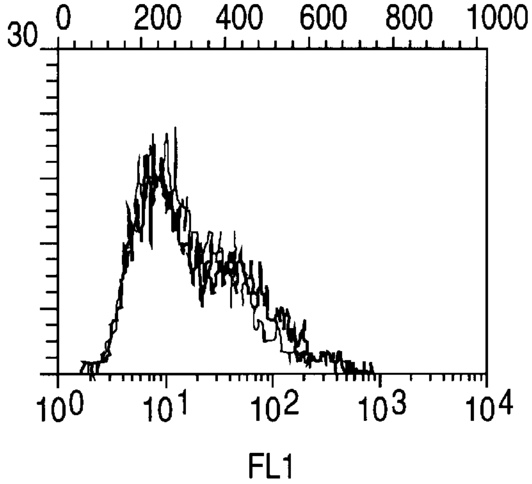
Figure 9C:
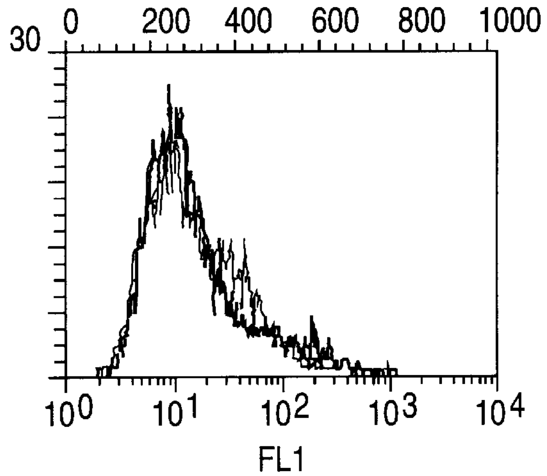
Figure 9D:
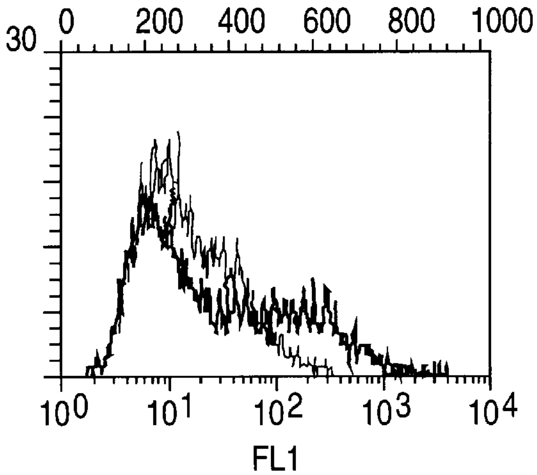

The Increase in Production of CD46(BC1) Caused by Silent Nucleotide Substitutions does not Appear to be Due to Increases in Expression of mRNA or of Transfected DNA Total RNA was prepared from populations of cells transfected with the various constructs and level of mRNA expression was determined by Northern blot (FIG. 7). The level of mRNA in total RNA was similar for constructs containing the silent mutations compared with the level for the unmutated wtSCR construct (FIG. 7). This level of expression represents that of the total cell population and does not indicate the level of expression per cell. The amount of plasmid present in the population of cells was determined by Southern blotting (FIG. 8) and was not significantly different for any of the constructs.

Silent Nucleotide Substitutions Increase the Production of CD46(BC1) in a Stable Transfection System After transfection and G418 drug selection, CHO-K1 transfectants were analysed by flow cytometry. Populations of selected cells transfected with constructs containing silent mutations contained more cells expressing CD46 and they expressed CD46 to a much a higher level (FIG. 9), with the greatest increase observed for the subSCR2+3 construct (panel D).

EXAMPLE 2

Preparation of mutagenised CD55 constructs.

A particular example for application of the invention can be provided by the nucleic acid encoding CD55 (DAF: Decay Accelerating Factor), a structurally related RCA molecule. The CD55 gene has AT-nucleotide rich regions within exons encoding the SCR2, SCR3 and SCR4 modules of CD55. Silent nucleotide substitutions are directed individually toward the sequences included within residues 388 to 412 (encoding SCR2); 590 to 602, 633 to 645 and 658 to 674 (encoding SCR3); 718 to 728 and 844 to 854 (encoding SCR4). The particular PCR primers for mutagenesis are designed to reduce the A and/or T content of the codons for these regions without altering the predicted amino acid sequence, which would be clear to one skilled in the art, but have sufficient lengths of sequence complementary to the cDNA template to enable priming of the initial PCR. Numbering of the CD55 gene is according to FIG. 3 of Lublin and Atkinson (Curr Top Micro Immunol 153, 123, 1989). These primers are designed in complementary pairs (forward and reverse primers in 5' and 3' directions) to allow annealing of the mutated PCR products in the Splice-Overlap Extension PCR as described specifically above. Additional forward and reverse PCR primers are designed, containing restriction enzyme cleavage sites, which anneal to the wildtype cDNA template at positions flanking the 5'-UTR and 3' of putative polyadenylation signals in the 3'-UTR, as is obvious to one skilled in the art. The six AT-rich sequences identified and listed above may variously accord with the requirements for augmented production of the protein in transfected cells. Each mutated construct is created individually, and combinations including multiple mutated spans of nucleotide sequence can be additionally prepared.

The PCR products are purified and cloned into the SK vector for complete sequencing to confirm integrity of the required mutated sequence, before cloning into the appropriate expression vector (e.g., pcDNA1) and transfection into eukaryotic cells. Production of the CD55 protein is assessed by flow cytometry using the IH4 anti-CD55 monoclonal antibody, and the relative expression of CD55 in transfected cells is correlated with the mutagenised construct. Thus the hierarchy of mutations affecting protein translation can be constructed.

Cells transfected with the optimal constructs are further tested for protection against complement-mediated lysis mediated by the expressed CD55, as decay-accelerating activity. This assay proves that the protein is appropriately expressed and is functioning normally.

EXAMPLE 3

Summary of CD46-Transfection Data

Nucleotide constructs, either of wild-type or mutated (substitution) forms, were cloned into the expression vectors: pcDNA1 (as already described); and APEX-3.

These expression constructs were transfected into cultured mammalian cell lines. Transfections were repeated to ensure that any variations in expression recorded were consistent and not erratic artefacts. The pcDNA1 vector constructs in COS-7 cells (transient expression) were variously expressed, depending on the silent nucleotide mutations in the particular CD46 constructs. This effect was consistent both for constructs encoding cell surface CD46 and constructs encoding soluble CD46. Other cell lines were tested for expression of wild-type and mutated constructs: mutation improved cell-surface CD46 protein expression in transiently transfected WOP-3027 cells, and in stably transfected CHO-K1 cells. Soluble protein was also produced with consistent and predictable expression in human 293 and 293-Ebna cells. Therefore, the effect of the mutation is not limited to COS-7 African Green monkey kidney fibroblast-like cells, but also is seen in WOP-3027 (polyoma virus-transformed) mouse embryonal fibroblast cells, CHO-K1 hamster ovary cells, and 293 (human embryonal kidney) cells. It is therefore likely that the effects will be observed in other cells also.

To assess the effect of the vector upon the expression of mutated constructs, forms encoding soluble CD46 were cloned into the APEX-3 vector. Mutation-dependent enhanced expression was seen in COS-7 and 293 (human embryonal kidney) cells, demonstrating that the effect was not limited to one vector.

Table II shows cell surface and soluble CD46 expression levels obtaining by transfection using a range of vectors, cell lines and constructs. The "±" symbol indicates basal, wild type expression levels and the number of "+" symbols shown for each test is directly proportional to the level of CD46 expression.

EXAMPLE 4

Studies of Translation Rate in Cell-free Translation Systems.

Figure 10:
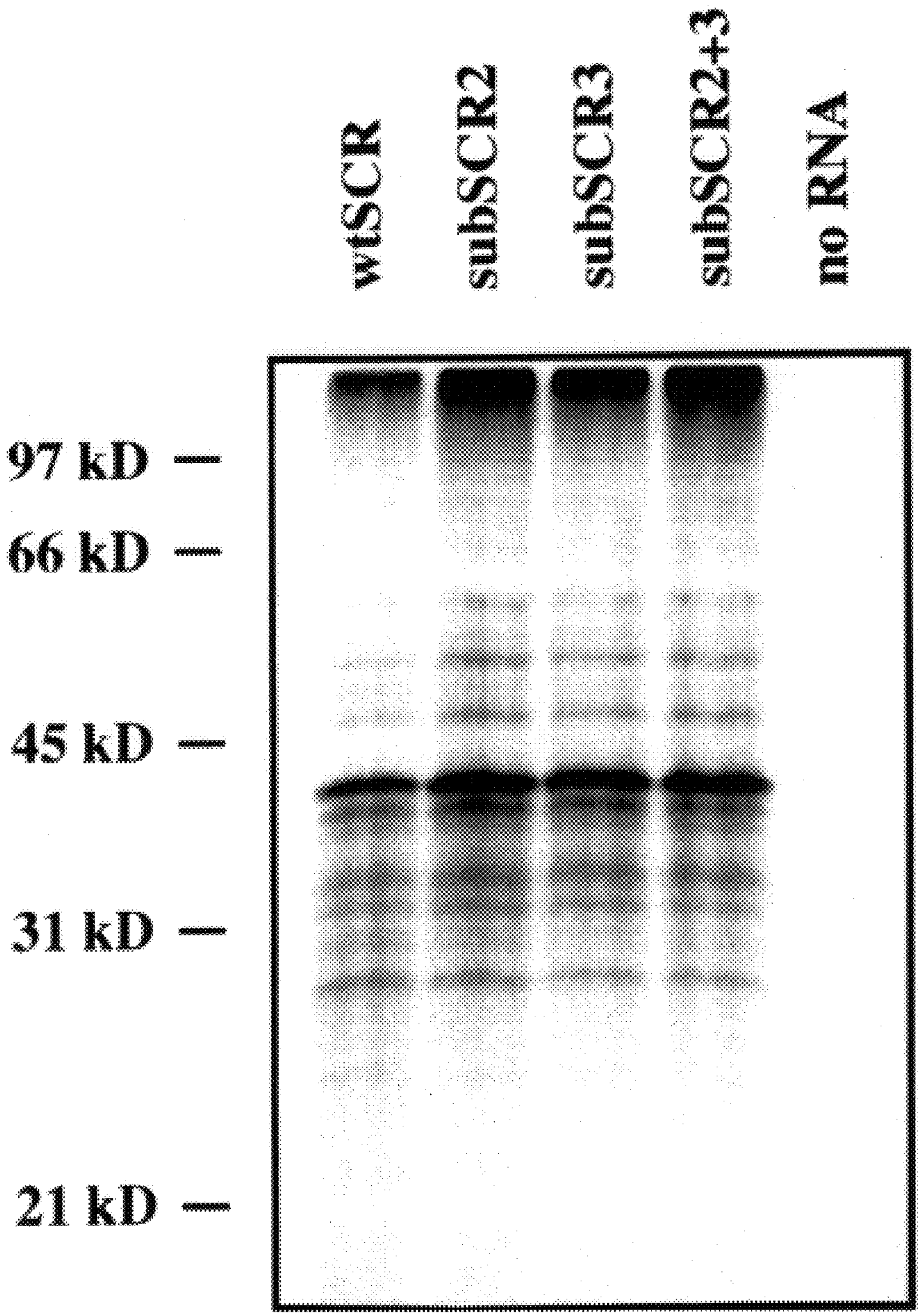
FIG. 10. In vitro translation of synthetic CD46 transcripts. Lanes contain 35S-methionine labelled in vitro translation products from capped mRNAs as labelled. The arrow indicates the non glycosylated protein of the expected size, and the molecular weight markers are shown.

CD46 synthetic wildtype and mutant transcripts were translated in vitro in a cell-free translation system containing rabbit reticulocytes (see FIG. 10). The lanes containing equal quantities of RNA transcribed from wtSCR, subSCR2, subSCR3 and subSCR2+3 DNA sequences all produced a similar amount of protein, showing that translation proceeded with equivalent efficiency regardless of the sequence of the transcript. The protein was of the expected size for nonglycosylated CD46 (38–40 kD).

EXAMPLE 5

Enhanced Expression of Soluble CD46 in CHO-K1, WOP-3027 and 293 Cells.

Figure 11:
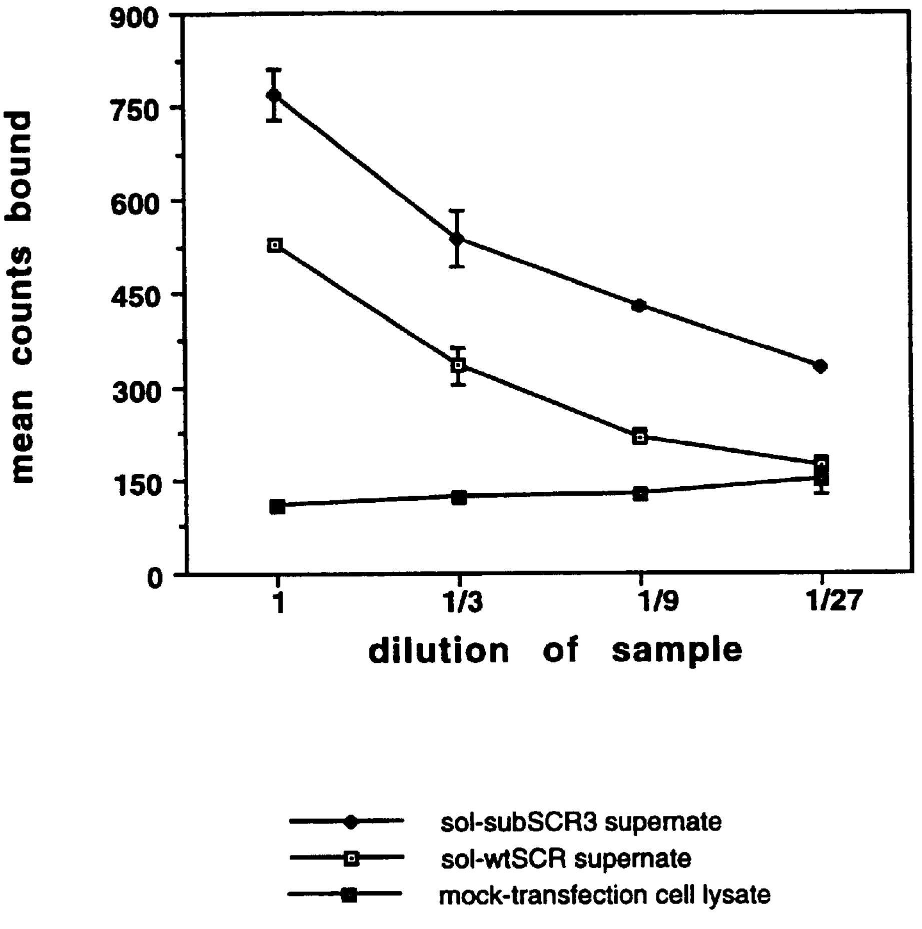
FIG. 11. Semi-quantitative radioimmunoassay (see Materials and Methods) of CHO-K1 cell lysates. An equivalent number of transfected cells was used for each sample. The mean number of counts bound (duplicates) with standard error is shown against dilution factor. The titration curves are for lysates of mock (■), soluble wtSCR (□) and soluble subSCR3 (●) transfected cells.

The soluble wtSCR and soluble subSCR3 constructs were transfected into WOP, CHO-K1 and 293 cells. An almost identical trend was observed when supernatants collected from transfected WOP cells were semi-quantitated by radioimmunoassay. Serum free supernatants from CHO cells collected 96 hours after transient transfection with soluble subSCR3, showed a 4-fold increase in protein expression (see FIG. 11). This was consistent with the increase observed when a parental stable CHO cell line expressing surface CD46 was established after cotransfection with soluble subSCR2+3 and pgKNeopA. Serum free supernatants from 293 cells were collected 6 days after transfection, and semi-quantitated by dot blotting, more protein (typically 3-fold) was observed when the construct containing silent nucleotide changes (soluble subSCR3) was used. These data clearly show the increase in soluble CD46 protein produced after transfection with a mutated construct, was not restricted to COS-7 cells.

EXAMPLE 6

Enhanced Expression of Soluble CD46 Using APEX-3 Expression Plasmids

Inserts encoding CD46 were ligated into the APEX-3 expression plasmid, and the two constructs; APEX3-sol-wtSCR and APEX3-sol-subSCR3 transfected into COS-7 & 293 cells. Serum free supernatants were collected 6 days after transfection, and semiquantitated by dot blotting. An increase in protein expression (typicall 3-fold) was observed when cells were transfected with the construct containing silent nucleotide changes (APEX3-sol-subSCR3). The data confirm that the observed increase in protein expression was not plasmid specific.

EXAMPLE 7

Studies to Determine Mechanism of Enhanced Protein Expression.

a) Transiently transfected COS cells contain similar quantities of plasmid DNA whether transfected with CD46 constructs consisting of mutated (silent nucleotide substituted) or wildtype sequences, as measured by Southern blot analyses. Therefore, the significant increase in production of CD46 protein is most likely due to transcriptional or translational regulation, and not due to altered efficiency of transfection, DNA stability, or plasmid DNA replication.

(b) COS cells transfected with mutated or wildtype CD46 plasmid constructs have equivalent quantities of CD46 mRNA but different quantities of CD46 protein. In two constructs (subSCR3 and subSCR2+3), a cryptic polyadenylation signal has been removed, which might have generated truncated mRNA species (in wildtype, delSCR2 or subSCR2 constructs). However, no truncated mRNA species are seen in Northern blots, and no differences in mRNA quantity, which might have been ascribed to altered mRNA stability or half-life, are observed. Therefore, the increased CD46 protein is most likely generated by regulation of translation.

(c) In vitro translation, using as template equivalent amounts of mRNA isolated from each of the transfected COS cells, generates equivalent quantities of CD46 protein whereas up to a 20-fold increase in cell-surface protein expression is reproducibly found in transfected COS cells. This focuses attention on the mechanism of protein translation, as it appears to be limited to specifically occurring within intact cells.

(d) To determine whether the increase in CD46 production was due to protein COS-7 cells were separately transfected with wtSCR, subSCR2+3 or subSCR3, biosynthetically labelled with 35S-Cys and 35S-Met, and CD46 protein was immunoprecipitated from cell lysates and supernatants and examined by SDS-PAGE. Cells transfected with subSCR2+3 synthesised more labelled CD46 than than those transfected with wtSCR. There was no CD46 protein detectable in the supernatant. Biosynthetically labelled CD46 was produced by cells transfected with solSCR3 and was secreted into the supernatant but, as expected, could not be detected in the lysate. Lysates and supernatants immunoprecipitated with an isotype control mAb, MEM-43, did not show any labelled material of the expected size.

EXAMPLE 8

The use of Mutagenised CD46 and CD55 Genes, Encoding Wildtype Protein, for the Production of Transgenic Animals.

Once the optimised mutant construct, such as the CD46 encoding SCR2+3 construct (see above) or the appropriate CD55 construct, has been proven by repeated transfection of eukaryotic cell lines in vitro, the DNA vector is highly purified to be suitable for transgenesis. The DNA (the transgene) is injected into fertilised mouse single-cell oocytes which are reimplanted into prepared pseudo-pregnant mice, entirely according to procedures familiar with those experienced in the art. The offspring are screened for integration of the transgene by Southern blotting DNA obtained from a small tissue sample, and founder mice are tested for transgene expression by Western blotting of a tissue cell lysate. Founders expressing the protein are bred and appropriately backcrossed to suitable mouse strains. Individual mice of each generation are also screened for protein expression of the transgene, and only expressing animals are used. Tissue samples from such transgenic mice are tested for function of the transgenic protein in complement-mediated lysis, complement-mediated graft rejection, and complement-mediated tissue inflammation assays, each of which is established and routine.

Only animals expressing sufficient amounts of the CD46 or CD55 transgenic protein on their cells to have augmented resistance to complement-mediated cell damage are kept to establish transgenic strains of mice. are kept to establish transgenic strains of mice.

Once function is confirmed using tissues of transgenic mice, which identifies the appropriate transgene DNA construct, the same transgenesis procedure is repeated using porcine oocytes, to produce transgenic pigs. The appropriate transgenic pigs are considered to be putative organ donors of xenogenic transplants for humans requiring kidney, heart, liver, pancreas, etc., grafts.

An important application of the invention is the genetic cross between transgenic animals expressing CD46 with transgenic animals expressing CD55, where co-expression of both molecules augments resistance to complement-mediated injury.

Although the above example relates to production of transgenic animals to provide donors of organ implants, transgenic animals containing the constructs of the present invention or whose cells produce proteins in accordance with the method of the invention, may be produced for other purposes. For example it may be desired to produce a transgenic cow which produces recombinant protein in its milk.

It is to be recognised that the present invention has been described by way of example only and that modifications and/or alterations which would be obvious to a person skilled in the art can be made thereto, without departing from the intended scope of the invention as defined in the appended claims.

TABLE I

Oligonucleotides and the combinations used to generate mutated CD46 constructs.

A. Oligonucleotide primers for PCR. (SEQ ID Nos: 7–15)

| PRIMER | SEQUENCE[a] | SIZE | ANNEALING POSITION[b] |
|---|---|---|---|
| On231 | 5'-CAATCAGGTAGTAACCCTCGTTGCAGATGAAGTGCATC-3' | 38-mer | nt 436–399 |
| On232 | 5'-cggaattcACAGCGTCTTCCGCGCCGCGC-3' | 29-mer | nt 4–32 |
| On233 | 5'-GGTCTTGTGTACACCACCTCCAAAGATCAAGAATGGAAAAC-3' | 41-mer | nt 510–550 |
| On238 | 5'-AGCAATGACCTAAACATCCAAACTGTC-3' | 27-mer | nt 1032–1006 |
| On239 | 5'-TGGATGTTTAGGTCATTGCTGTGATT-3' | 26-mer | nt 1013–1038 |
| On240 | 5'-GGTGTACACAAGACCTTATAACAGGCGTCATCTG-3' | 34-mer | nt 524–509/319–302 |
| On241 | 5'-acgaattcGATTTCAAGCCACTTTCTTTACAAAG-3' | 34-mer | nt 1641–1608 |
| On247 | 5'-GGTGGTGTACACAAGACCTTCTCACATATTGG-3' | 32-mer | nt 527–496 |
| On250 | 5'-CGAGGGTTACTACCTGATTGGTGAGGAGATCCTGTATTGTGAAC-3' | 44-mer | nt 417–460 |

B. Primer combinations for mutated CD46 constructs produced by PCR.

| MUTATED CONSTRUCT | 5' PCR FRAGMENT | 3' PCR FRAGMENT | TEMPLATE |
|---|---|---|---|
| subSCR2 | On232/On231 | On241/On250 | pm5.1 |
| subSCR3 | On232/On247 | On241/On233 | pm5.1 |
| subSCR2 + 3 | On232/On231 | On241/On250 | subSCR3 |
| delSCR2/subSCR3 | On232/On240 | On241/On247 | pm5.1 |
| sol-wtSCR | On232/On238 | On241/On239 | pm5.1 |
| sol-subSCR3 | On232/On247 | On241/On233 | sol-wtSCR |

[a]EcoRI restriction sites and overhang are shown in lower case; mutated nucleotides are in italics and bold font.
[b]Annealing position is based on pm5.1 (Purcell et al., 1991)

TABLE II

Cell surface and soluble CD46 expression obtained by transfection of constructs into various cell lines

| | Cell-surface CD46 Construct | | | | | Soluble-CD46 Construct | | | | |
|---|---|---|---|---|---|---|---|---|---|---|
| | wild-type | sub2 | sub3 | sub 2 + 3 | del2 sub3 | wild-type | sub3 | sub 2 + 3 | del2 sub3 | 1.8 mutant |
| pcDNA1 vector | | | | | | | | | | |
| COS-7 | ± | ++ | +++ | ++++ | ++++ | ± | ++ | ++ | +++ | +++ |
| 293 | | | | | | ± | + | ++ | | |
| 293-Ebna | | | | | | ± | + | ++ | | |
| WOP-3027 | ± | | | | +++ | ± | ++ | + | | |
| CHO-K1 | ± | + | ++ | +++ | +++ | | | | | |
| APEX-3 vector | | | | | | | | | | |
| COS-7 | | | | | | ± | ++ | ++ | | |
| 293 | | | | | | ± | ++ | ++ | | |

We claim:

1. A method of increasing production of mammalian CD46 protein in a host cell, wherein a nucleic acid encoding the CD46 protein has an A and/or T rich region containing more than 60% A and/or T in an exon, said method comprising the steps of:

altering the nucleic acid by reducing the amount of A and/or T in said region to less than 60% A and/or T;

transfecting a host cell with said altered nucleic acid, and obtaining expression of said altered nucleic acid under appropriate conditions, wherein the level of CD46 protein production resulting from expression of said altered nucleic acid is increased relative to the level of CD46 protein production resulting from expression of said nucleic acid before alteration; and wherein RNA stability of RNA produced from expression of said altered nucleic acid is not demonstrably altered relative to the stability of RNA produced from expression of said nucleic acid before alteration.

2. The method claim 1 wherein said altered nucleic acid is transfected into said host cell as a component of a recombinant nucleic acid construct.

3. The method of claim 1 wherein said altering of the nucleic acid is by effecting one or more silent mutations.

4. The method of claim 1 wherein said altering of the nucleic acid is by effecting one or more conservative mutations.

5. The method of claim 1 wherein said altering of the nucleic acid is by insertion of one or more nucleotides other than A or T.

6. The method of claim 1 wherein said altering of the nucleic acid is by deletion of one or more nucleotides other than A or T.

7. The method claim 1 wherein said altering of the nucleic acid is by a combination of any two or more of:

a. one or more silent mutations b. one or more conservative mutations c. insertion of one or more nucleotides other than A or T d. deletion of A and/or T deletion of A and/or T rich regions.

8. The method of claim 1 wherein said nucleic acid has A and/or T rich regions present in one or more of its short consensus repeat (SCR) modules.

9. The method of claim 8 wherein said nucleic acid is altered in one or more of its SCR modules.

10. The method of claim 1 wherein said altering of the nucleic acid is by deletion of one or more SCR modules or parts thereof.

11. The method of claim 1 wherein said altered nucleic acid comprises a nucleic acid selected from the group consisting of SEQ.ID.No. 2, SEQ.ID.No. 3, SEQ.ID.No. 4 and SEQ.ID.No. 5.

12. The method of claim 1 wherein said altered nucleic acid is transfected into a host cell as a component of a recombinant nucleic acid construct and said recombinant nucleic acid construct includes an eukaryotic vector.

13. The method of claim 1 wherein said altered nucleic acid is transfected into a host cell as a component of a recombinant nucleic acid construct and said host cell is an eukaryotic host cell.

14. The method of claim 1 wherein said altered nucleic acid is transfected into a host cell as a component of a recombinant nucleic acid construct and said host cell is COS-7 or CHO-K1.

15. The method of claim 1 wherein said A and/or T rich region contains approximately 78% A and/or T which is reduced or lowered to approximately 55% by altering the nucleic acid.

16. The method of claim 1 wherein said A and/or T rich region contain approximately 71% A and/or T which is reduced or lowered to approximately 58% by altering the nucleic acid.

17. A recombinant nucleic acid construct that provides for increased production of mammalian CD46 protein in a host cell, wherein said recombinant nucleic acid construct is formed by altering a nucleic acid encoding the CD46 protein and having an A and/or T rich region containing more than 60% A and/or T by reducing the amount of A and/or T in said region to less than 60% A and/or T, and wherein RNA stability of RNA produced from the expression of said altered nucleic acid is not demonstrably altered relative to the stability of RNA produced from expression of said nucleic acid before alteration.

18. A recombinant nucleic acid construct comprising a nucleic acid selected from the group consisting of SEQ.ID.No. 2, SEQ.ID.No. 3, SEQ.ID.No. 4 and SEQ.ID.No. 5.

* * * * *